(12) United States Patent
Belson et al.

(10) Patent No.: US 12,390,221 B2
(45) Date of Patent: *Aug. 19, 2025

(54) CLOSURE APPARATUSES AND METHODS FOR ULCERS AND IRREGULAR SKIN DEFECTS

(71) Applicant: ZipLine Medical, Inc., Campbell, CA (US)

(72) Inventors: Amir Belson, Savyon (IL); Keiichiro Ichiryu, Campbell, CA (US); Daren Stewart, Belmont, CA (US); Eric Storne, Menlo Park, CA (US)

(73) Assignee: Zipline Medical Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/515,669

(22) Filed: Nov. 21, 2023

(65) Prior Publication Data
US 2024/0090898 A1    Mar. 21, 2024

Related U.S. Application Data

(63) Continuation of application No. 17/269,786, filed as application No. PCT/US2019/048413 on Aug. 27, 2019, now Pat. No. 11,864,766.
(Continued)

(51) Int. Cl.
*A61B 17/08* (2006.01)

(52) U.S. Cl.
CPC ...... *A61B 17/085* (2013.01); *A61B 2017/081* (2013.01); *A61B 2017/086* (2013.01)

(58) Field of Classification Search
CPC ............ A61B 17/085; A61B 2017/081; A61B 2017/086; A61B 17/08; A61B 17/0466;
(Continued)

(56) References Cited

U.S. PATENT DOCUMENTS

| 5,665,108 A | 9/1997 | Galindo |
| 7,838,718 B2 | 11/2010 | Lebner |

(Continued)

FOREIGN PATENT DOCUMENTS

| JP | 2006-528513 | 12/2006 |
| JP | 2013-501591 | 1/2013 |

(Continued)

OTHER PUBLICATIONS

International Search Report mailed on Dec. 27, 2019, issued in connection with International Application No. PCT/US2019/048413, filed on Aug. 27, 2019, 4 pages.
(Continued)

*Primary Examiner* — Majid Jamialahmadi
(74) *Attorney, Agent, or Firm* — McDonnell Boehnen Hulbert & Berghoff LLP

(57) ABSTRACT

Devices, methods, and systems for treating an ulcer or skin defect are disclosed. First and second base panels of a closure device are adhered to first and second sides of the ulcer or skin defect, respectively. Lateral ties couple the first and second base panels together and provide a predetermined separation distance or lateral gap between the inner edges of the panel. The predetermined separation distance or lateral gap is sufficient to treat the most common sized ulcers or skin defects, for example, accommodating an ulcer or skin defect with a minor axis of at most 50 mm. The lateral ties have their ends fixed to one panel and their opposite ends adjustably and reversibly attached to the other panel so that the separation distance can be reduced or adjusted to provide a lateral compressive force to the ulcer or skin defect, thereby promoting healing.

20 Claims, 17 Drawing Sheets

Related U.S. Application Data

(60) Provisional application No. 62/725,705, filed on Aug. 31, 2018.

(58) Field of Classification Search
CPC ........... A61B 2017/088; A61F 13/0253; A61F 2013/00451
See application file for complete search history.

(56) References Cited

U.S. PATENT DOCUMENTS

| | | |
|---|---|---|
| 8,232,313 B2 | 7/2012 | Munn et al. |
| 8,313,508 B2 | 11/2012 | Belson et al. |
| 8,439,945 B2 | 5/2013 | Belson et al. |
| 8,592,640 B2 | 11/2013 | Zepeda et al. |
| 9,050,086 B2 | 6/2015 | Belson et al. |
| 9,089,328 B2 | 7/2015 | Belson et al. |
| 9,179,914 B2 | 11/2015 | Belson et al. |
| 9,474,529 B2 | 10/2016 | Belson et al. |
| 9,554,799 B2 | 1/2017 | Belson et al. |
| 9,554,800 B2 | 1/2017 | Belson et al. |
| 9,561,034 B2 | 2/2017 | Belson et al. |
| 9,624,621 B2 | 4/2017 | Irnich et al. |
| 9,624,622 B2 | 4/2017 | Müller et al. |
| 10,010,710 B2 | 7/2018 | Belson et al. |
| 10,123,800 B2 | 11/2018 | Belson et al. |
| 10,123,801 B2 | 11/2018 | Belson et al. |
| 10,159,825 B2 | 12/2018 | Belson et al. |
| 10,456,136 B2 | 10/2019 | Belson et al. |
| 10,888,269 B2 | 1/2021 | Belson et al. |
| 2003/0092969 A1 | 5/2003 | O'Malley et al. |
| 2005/0020957 A1 | 1/2005 | Lebner |
| 2006/0058842 A1 | 3/2006 | Wilke et al. |
| 2013/0296930 A1 | 11/2013 | Belson et al. |
| 2013/0331757 A1 | 12/2013 | Belson |
| 2014/0058444 A1 | 2/2014 | Fox |
| 2014/0171849 A1* | 6/2014 | Fischell ............. A61F 13/0246 602/53 |
| 2015/0051530 A1* | 2/2015 | Noda ................... A61B 17/085 602/41 |
| 2015/0216527 A1 | 8/2015 | Belson et al. |
| 2015/0223814 A1 | 8/2015 | Nash et al. |
| 2016/0249924 A1 | 9/2016 | Belson |
| 2017/0035422 A1 | 2/2017 | Belson et al. |
| 2017/0156664 A1 | 6/2017 | Belson et al. |
| 2018/0070878 A1 | 3/2018 | Kamakura et al. |
| 2018/0214148 A1 | 8/2018 | Christiansen et al. |
| 2019/0254673 A1* | 8/2019 | Nezu ................... A61B 17/085 |

FOREIGN PATENT DOCUMENTS

| | | |
|---|---|---|
| JP | 2015-516820 | 11/2017 |
| WO | 2010/093753 A1 | 8/2010 |
| WO | 2014021934 | 2/2014 |
| WO | 2017/000758 A1 | 1/2017 |
| WO | 2017/184825 A1 | 10/2017 |
| WO | WO 2017/181059 A1 | 10/2017 |
| WO | 2017200058 | 11/2017 |
| WO | WO 2018/082178 A1 | 5/2018 |

OTHER PUBLICATIONS

Written Opinion mailed on Dec. 27, 2019, issued in connection with International Application No. PCT/US2019/048413, filed on Aug. 27, 2019, 9 pages.

\* cited by examiner

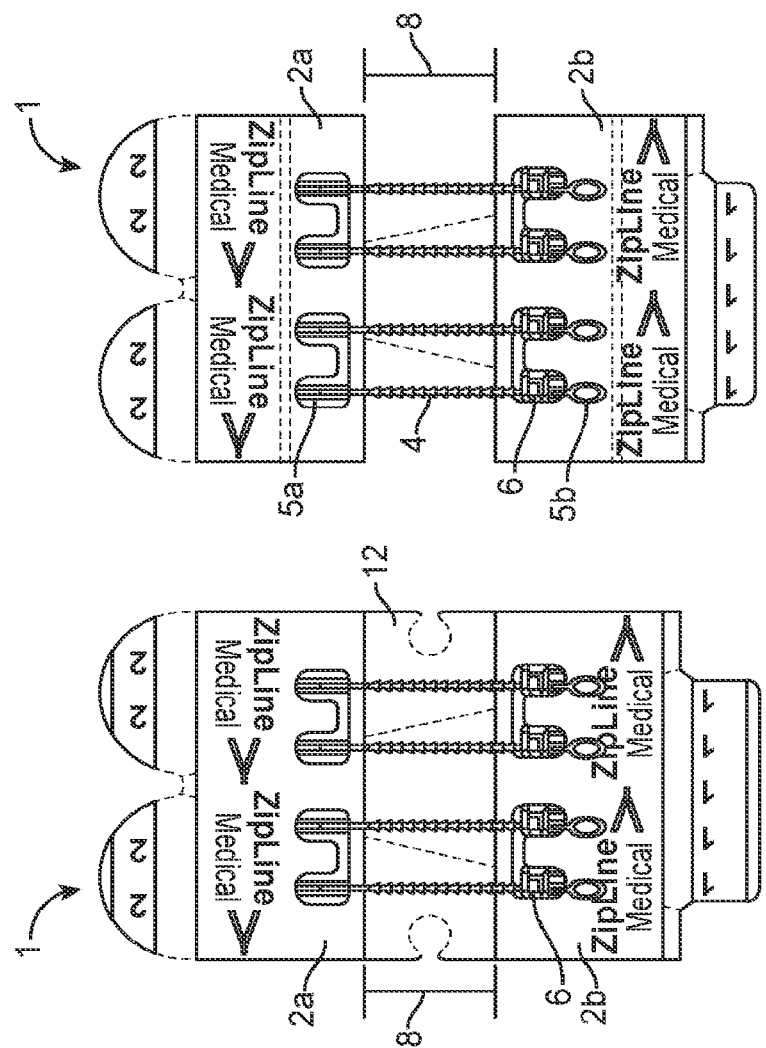
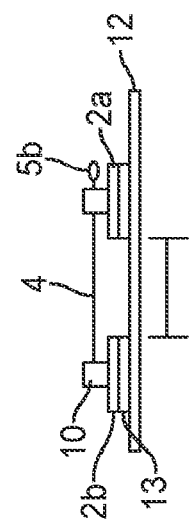
FIG. 1A  FIG. 1B  FIG. 1C

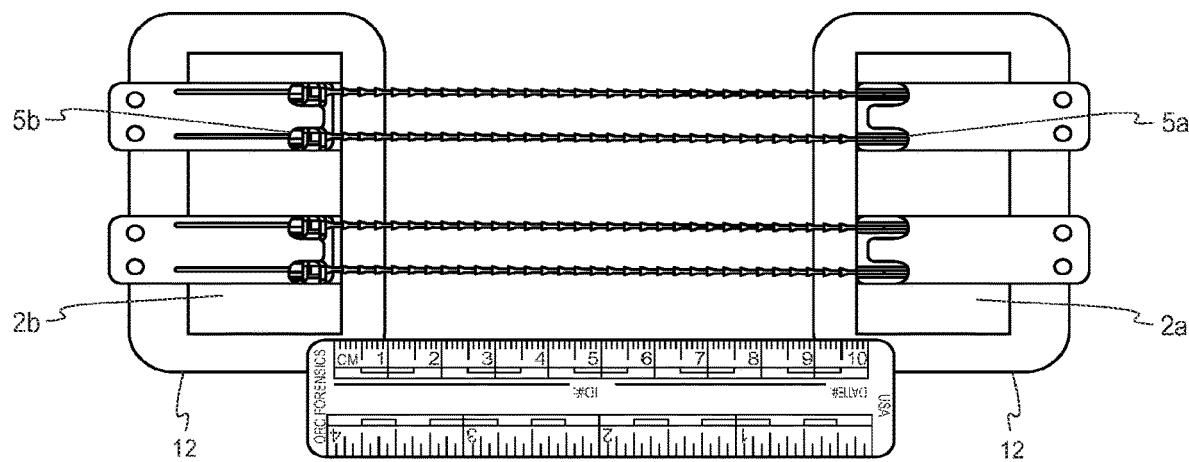
FIG. 2A
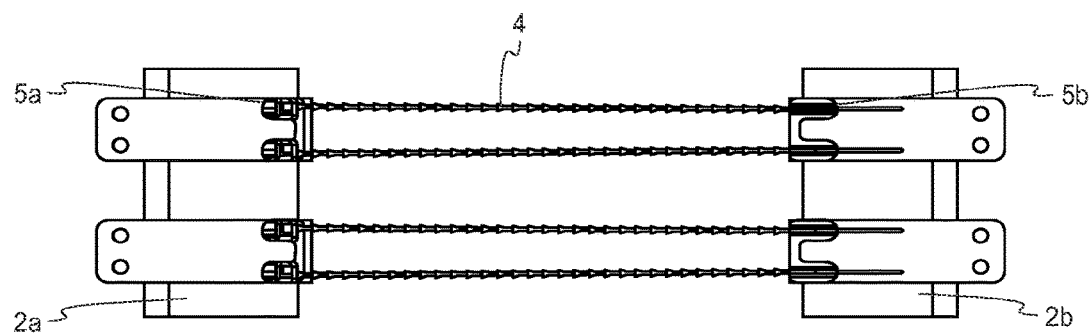
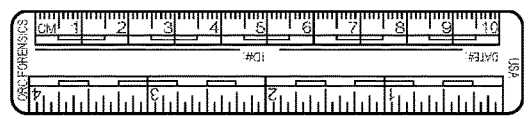
FIG. 2B

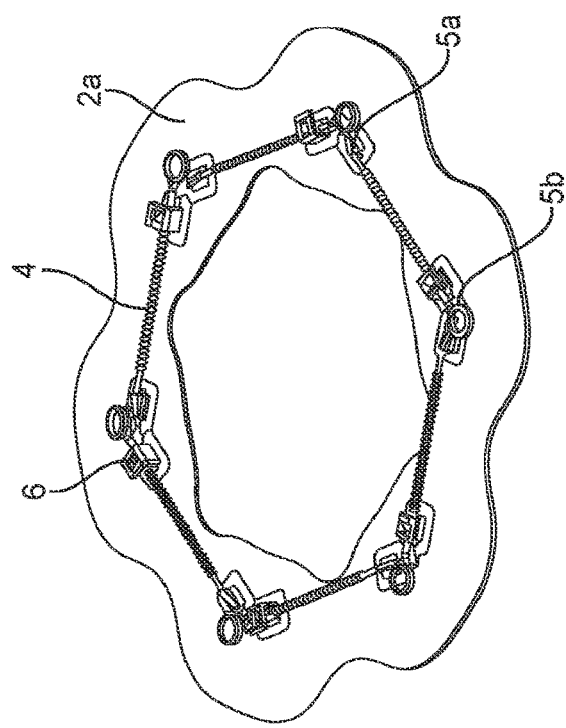
FIG. 9A
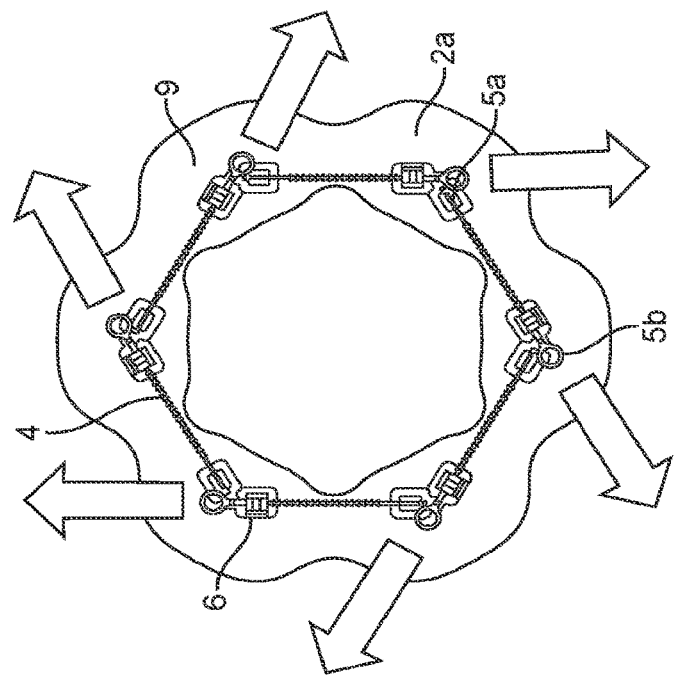
FIG. 9B
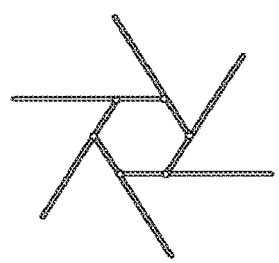
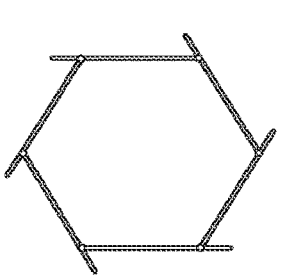
FIG. 9C

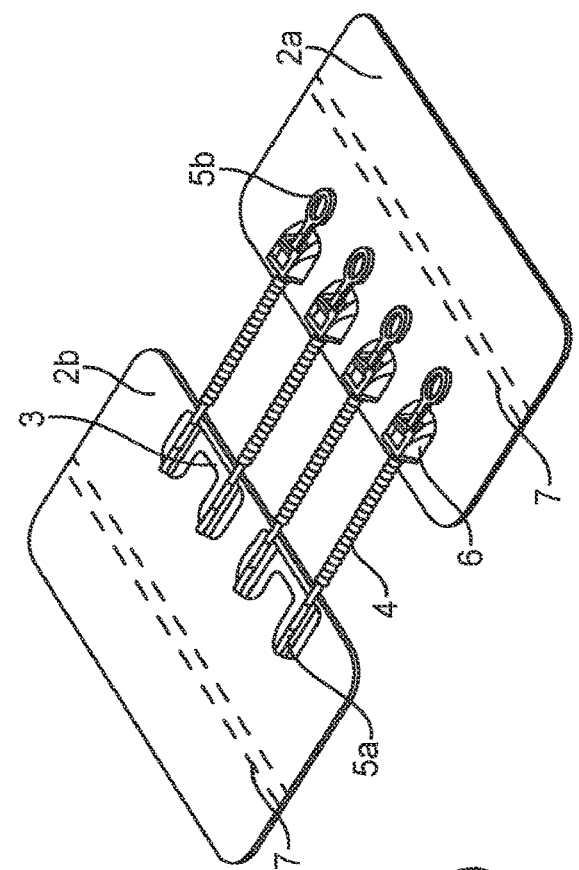
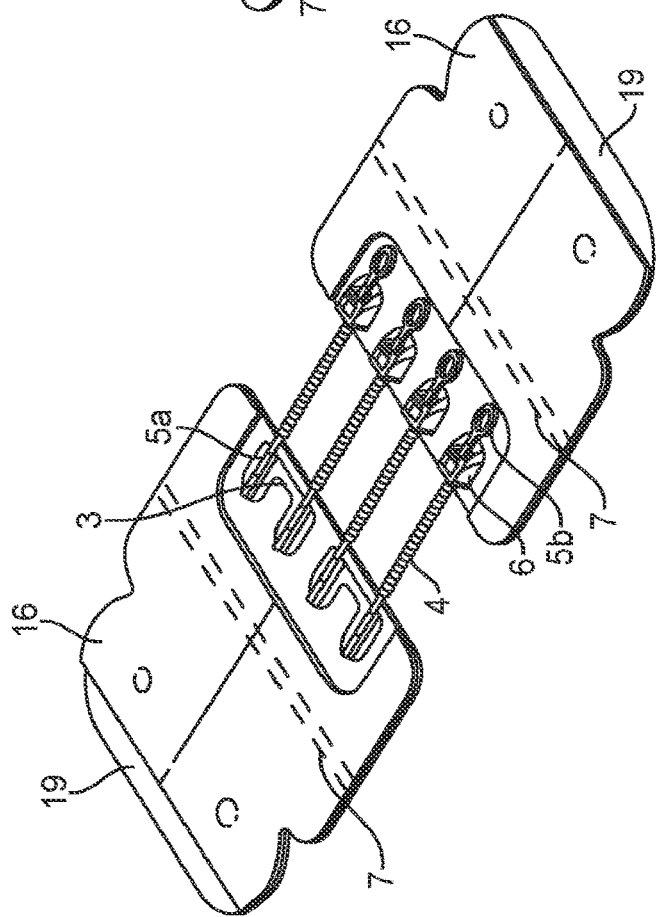
FIG. 12A
FIG. 12B

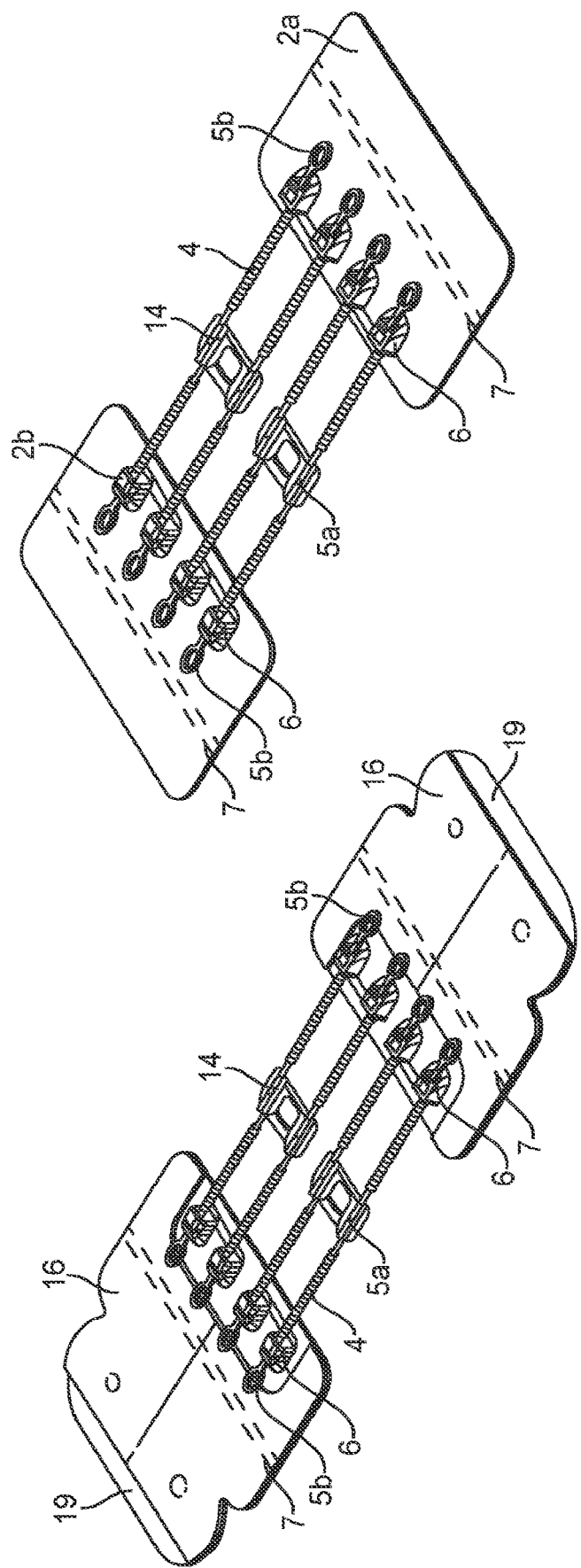

CLOSURE APPARATUSES AND METHODS FOR ULCERS AND IRREGULAR SKIN DEFECTS

CROSS-REFERENCE

This application is a continuation of U.S. patent application Ser. No. 17/269,786, filed Feb. 19, 2021, which is a national stage entry under 35 U.S.C. § 371 of International Application No. PCT/US/2019/048413, filed Aug. 27, 2019, which claims priority to provisional patent application U.S. Ser. No. 62/725,705, filed Aug. 31, 2018, which are incorporated herein by reference in their entirety. The subject matter of the present application is related to the subject matter in the following U.S. Patent Applications: U.S. patent application Ser. No. 13/286,757 (now U.S. Pat. No. 8,323,313), Ser. Nos. 13/665,160, 14/180,524 (U.S. Pat. No. 9,050,086), Ser. Nos. 14/180,564, 14/625,366 (U.S. Pat. No. 9,642,621), Ser. No. 15/081,526 (U.S. Pat. No. 9,474,529), Ser. No. 15/081,550 (U.S. Pat. No. 9,554,799), Ser. No. 15/081,595 (U.S. Pat. No. 9,642,622), Ser. No. 15/096,083 (U.S. Pat. No. 9,554,800), Ser. No. 15/130,149 (U.S. Pat. No. 9,561,034), and Ser. No. 15/369,293, and Provisional patent application U.S. Ser. No. 62/725,705, and PCT Application Nos. PCT/US2015/028066, PCT/US2016/028297, and PCT/US2017/028537, which are incorporated herein by reference in the entirety.

BACKGROUND

The present disclosure is directed to medical devices, methods, and systems, particularly for aiding the closure and healing of wounds and incisions, specifically ulcers and irregular skin defects.

Staples and sutures have been in use for many years to close wounds and incisions. Staples and sutures, however, may be less than ideal for use with certain wounds and incisions, for example, because of their irregular shape or the concentration of closure forces on certain areas of tissue from the staples or sutures, which may lead to additional scarring or less than optimal healing. Also, once in place, staples and sutures may be difficult to adjust and reverse, such as when re-approximation of the edges of the wound or incision (i.e., bringing together in good alignment) needs to be adjusted. In many such cases, liquid glue, commonly cyanoacrylate, may be used alone or in combination with staples, sutures, simple tape strips, or a mesh placed over the wound or incision. The liquid glue may cure or harden over the wound or incision to hold it in place and at least partially protect it from the external environment. Once cured, however, liquid glue can be very rigid. When exposed to lateral forces, blistering and adhesion loss at the border of the cured glue and the uncovered skin may result. The cured glue may also crack, exposing the underlying wound or incision. Hence, improved devices, methods, and systems for aiding the closure and healing of wounds and incisions may be desired.

SUMMARY

The present disclosure provides improved medical devices, methods, and systems for aiding the closure and healing of wounds and incisions, specifically ulcers and irregular skin defects.

Disclosed herein are methods for treating an ulcer or skin defect. An exemplary method comprises the steps of adhering a first panel of a closure device to skin on a first side of an ulcer or skin defect, adhering a second panel of the closure device to skin on a second side of the ulcer or skin defect, wherein the first and second panels have a separation distance between inside lateral edges thereof, the separation distance being at least 10 mm, and laterally compressing the ulcer or skin defect between the first and second panels, thereby reducing the separation distance between the inside lateral edges of the first and second panels.

The methods disclosed herein may be suitable to treat ulcers and skin defects with a variety of shapes and sizes. The ulcer or skin defect can have a minor axis of at most 50 mm. The ulcer or skin defect can have a minor axis of at most 40 mm. The ulcer or skin defect can have a minor axis of at most 30 mm. The ulcer or skin defect can have a minor axis of at most 20 mm. The ulcer or skin defect can have a minor axis of at most 10 mm. The separation distance between the inside lateral edges of the first and second panels prior to laterally compressing the ulcer or skin defect can be at least 20 mm. The separation distance between the inside lateral edges of the first and second panels prior to laterally compressing the ulcer or skin defect can be at least 30 mm.

The method can further comprise removing one or more liners from the closure device prior to adhering the first and second panels to the skin. The one or more liners can be aligned in an orientation transverse to longitudinal axes of the first and second panels. The method can further comprise removing a middle liner prior to adhering the closure device to the skin and removing one or more further liners adjacent the middle liner. The method can further comprise removing one or more liners adjacent a middle liner prior to adhering the closure device to the skin and removing the middle liner. The method can further comprise removing a first liner from the first base panel prior to adhering the closure device to the skin and removing a second liner from the second base panel.

The method can further comprise adhering the first and second panels to the skin comprises pressing adhesive bottom layers of the first and second panels against the skin. The adhesive bottom layers of the first and second panels can comprise a hydrocolloid adhesive. The first and second panels can comprise base layers positioned over the hydrocolloid adhesives, the base layers being more rigid than the hydrocolloid adhesive. The first and second panels each can further comprise one or more force distribution structures coupled to the base layers, the force distribution structures being more rigid than the base layers.

The method can further comprise one or more lateral ties coupling the first and second base panels to one another. The one or more lateral ties can be at least partially elastic. The one or more lateral ties can comprise an elastic or spring component. The method can further comprise disengaging the one or more lateral ties from one or more of the first or second base panels to provide access to the ulcer or skin defect for care. The method can further comprise re-engaging the one or more lateral ties to the one or more of the first or second base panels after the care. The care can comprise one or more of a cleaning, a debridement, an application of medication, an application of a skin substitute, an application of negative pressure, or an application of an oxygen-introducing apparatus to the ulcer or skin defect. Laterally compressing the ulcer or skin defect can comprise adjusting one or more attachment points of one or more lateral ties to the first or second panels. The ulcer or skin defect can be a diabetic foot ulcer, a venous leg ulcer, an arterial ulcer, a dehisced wound, a dehisced infection, a fasciotomy, a pressure or decubitus ulcer, or a biopsy incision.

The method can further comprise adhering the first and second panels of the closure device positions the closure device over the ulcer or skin defect in a first orientation, and wherein the method further comprises positioning a second closure device over the ulcer or skin defect in a second orientation different from the first orientation and adhering base panels of the second closure device to the skin on third and fourth sides of the ulcer or skin defect.

The method can further comprise further reducing the separation distance between the inside lateral edges of the first and second panels after the ulcer or skin defect has at least partially healed. The method can comprise further reducing the separation distance between the inside lateral edges of the first and second panels after the ulcer or skin defect has at least partially healed comprises incrementally tightening one or more lateral ties coupling the first and second base panels to one another over a period of time to restore or increase a compressive force to promote healing of the ulcer or skin defect.

One or more of the first or second base panels can have a lateral elasticity gradient of increasing elasticity from an inner edge thereof to an outer edge thereof. The lateral elasticity gradient can be provided by one or more of overlapping materials of different elasticity, stepped layers of material of a same elasticity, embossing, perforating, or patterning with areas of no material to the one or more of the first or second base panel. One or more of the first or second base panels can have a vertical elasticity gradient of increasing elasticity from an upper surface thereof to a bottom surface thereof. The vertical elasticity gradient can be provided by vertically overlapping layers of different elasticity or thickness. One or more of inner or outer edges of one or more of the first or second base panels can be sinusoidal or scalloped to minimize or distribute shear force or minimize skin blister formation.

Disclosed herein are closure devices for treating an ulcer or skin defect. An exemplary closure device comprises a first panel having a first adhesive bottom surface for adhering to skin on a first side of an ulcer or skin defect, a second panel having a second adhesive bottom surface for adhering to skin on a second side of the ulcer or skin defect, a plurality of lateral ties coupling the first and second panels to one another, the plurality of lateral ties maintaining a separation distance of at least 10 mm between inside lateral edges of the first and second panels, and one or more liners coupled to the first and second adhesive bottom surfaces.

The separation distance can be at least 20 mm. The separation distance can be at least 30 mm. The separation distance can be at least 40 mm. The separation distance can be at least 50 mm.

The one or more liners can be aligned in an orientation transverse to longitudinal axes of the first and second panels. The one or more liners can comprise a middle liner prior and one or more further liners adjacent the middle liner. The one or more liners can comprise a first liner removably coupled to the first adhesive bottom layer of the first base panel prior and a second liner removably coupled to the second adhesive bottom layer of the second base panel.

The first and second adhesive bottom layers of the first and second panels can comprise hydrocolloid adhesive. The first and second panels can comprise base layers positioned over the hydrocolloid adhesives, the base layers being more rigid than the hydrocolloid adhesive.

The first and second panels each can further comprise one or more force distribution structures coupled to the base layers, the force distribution structures being more rigid than the base layers. The one or more lateral ties can be at least partially elastic. The one or more lateral ties can comprise an elastic or spring component. The one or more lateral ties can be at least partially disengagable and re-engagable to provide access to the ulcer or skin defect for care. The one or more lateral ties can be at least partially adjustable to reduce the separation distance between the inside lateral edges of the first and second panels and apply a compressive force to tissue therebetween when the device is adhered to skin.

The one or more of the first or second base panels can have a lateral elasticity gradient of increasing elasticity from an inner edge thereof to an outer edge thereof. The lateral elasticity gradient can be provided by one or more of overlapping materials of different elasticity, stepped layers of material of a same elasticity, embossing, perforating, or patterning with areas of no material to the one or more of the first or second base panel. The one or more of the first or second base panels can have a vertical elasticity gradient of increasing elasticity from an upper surface thereof to a bottom surface thereof. The vertical elasticity gradient can be provided by vertically overlapping layers of different elasticity or thickness. The one or more of inner or outer edges of one or more of the first or second base panels can be sinusoidal or scalloped to minimize or distribute shear force or minimize skin blister formation.

Disclosed herein are closure devices for treating an ulcer or skin defect. An exemplary closure device comprises an adhesive bottom layer, a base layer, a plurality of supports coupled to the base layer; and a plurality of adjustable ties coupled to the plurality of supports, wherein the adhesive bottom layer and the base layer define a central treatment aperture to accommodate the ulcer or skin defect, and wherein the plurality of adjustable ties are adjustable to reduce an area of the central treatment aperture and apply a compressive force tissue encompassed by the central treatment aperture thereby.

Each lateral tie can comprise a fixed end and an adjustable end. The lateral ties can be arranged end-to-end along a periphery of the closure device. The fixed ends of the lateral ties can be adjacent adjustable ends of the lateral ties. The device can further comprise a central hub structure. The fixed ends of the lateral ties can be coupled to the central hub structure and the adjustable ends of the lateral ties are coupled to the supports coupled to the base layer.

The bottom layer can comprise a hydrocolloid adhesive. The main layer can be positioned over the hydrocolloid adhesive and is more rigid than the hydrocolloid adhesive. The plurality of supports can be more rigid than the base layers. The one or more lateral ties can be at least partially disengagable and re-engagable.

The device can have a lateral elasticity gradient of increasing elasticity from an inner edge thereof to an outer edge thereof. The lateral elasticity gradient can be provided by one or more of overlapping materials of different elasticity, stepped layers of material of a same elasticity, embossing, perforating, or patterning with areas of no material to the one or more of the first or second base panel. The device can have a vertical elasticity gradient of increasing elasticity from an upper surface thereof to a bottom surface thereof. The vertical elasticity gradient can be provided by vertically overlapping layers of different elasticity or thickness. The one or more of inner or outer edges of one or more of the first or second base panels can be sinusoidal or scalloped to minimize or distribute shear force or minimize skin blister formation. The device can have a triangular, rectangular, square, pentagonal, hexagonal, or other polygonal outer shape.

Disclosed herein are methods for treating an ulcer or skin defect. An exemplary method may comprise the steps of positioning a closure device over the ulcer or skin defect so that the ulcer or skin defect is encompassed by the central treatment aperture of the closure device, adhering the closure device to skin around the ulcer or skin defect, and tightening one or more adjustable ties of the closure device to apply a compressive force to tissue to tissue around the ulcer or skin defect encompassed by the central treatment aperture.

Each lateral tie can comprise a fixed end and an adjustable end. The lateral ties can be arranged end-to-end along a periphery of the closure device. The fixed ends of the lateral ties can be adjacent adjustable ends of the lateral ties. The closure device further can comprise a central hub structure. The fixed ends of the lateral ties can be coupled to the central hub structure and the adjustable ends of the lateral ties are coupled to the supports coupled to the base layer. The ulcer or skin defect can be a diabetic foot ulcer, a venous leg ulcer, an arterial ulcer, a dehisced wound, a dehisced infection, a fasciotomy, a pressure or decubitus ulcer, or a biopsy incision. The ulcer or skin defect can have a minor axis of at most 30 mm. The ulcer or skin defect can have a minor axis of at most 20 mm. The ulcer or skin defect can have a minor axis of at most 10 mm.

Wound closure devices described herein may comprise a pair of flexible, adhesive panels placed on opposite sides of the wound or incision. Lateral ties couple the panels together and separate the panels to provide enough space for the panels to encompass an ulcer or irregular skin defect. Once the closure device is adhered onto the skin adjacent the ulcer or irregular skin defect, the lateral ties may then be tightened to close the separation distance between the panels and apply an inwardly compressive force to promote healing.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

| Drawing Element | Reference Number |
| --- | --- |
| Closure apparatus | 1 |
| Base panel | 2a |
| Base panel | 2b |
| Force distribution structure elements | 3 |
| Lateral tie | 4 |
| Lateral tie fixed end | 5a |
| Lateral tie adjustable end | 5b |
| Locks | 6 |
| Perforations | 7 |
| Lateral gap | 8 |
| Single base | 9 |
| Force distribution structure | 10 |
| Middle layer/main body | 11 |
| Release liner | 12 |
| Adhesive layer | 13 |
| Elastic component | 14 |
| Open wound | 15 |
| Casting sheet | 16 |
| Closure element | 17 |
| Closure element fixed end | 18a |
| Closure element adjustable end | 18b |
| Tab of release liner | 19 |
| Wound aperture | 20 |
| Central hub structure | 21 |

FIG. 1A shows a top view of a closure apparatus, according to embodiments of the present disclosure.

FIG. 1B shows another top view of the closure apparatus of FIG. 1A.

FIG. 1C shows a side view of the closure apparatus of FIG. 1A.

FIG. 2A shows a top view of a wide closure apparatus, according to embodiments of the present disclosure.

FIG. 2B shows a top view of the wide closure apparatus of FIG. 2A with the device liner removed.

FIG. 3A show a top view of the wound or skin defect.

FIG. 3B shows the closure apparatus with a liner removed.

FIG. 3C shows the closure apparatus with the liner removed placed over the wound or skin defect.

FIG. 3D shows the closure apparatus with the remaining liners removed; the closure apparatus is pressed and adhered to the skin around the wound or skin defect.

FIG. 3E shows the closure apparatus adhered to the skin and having its lateral ties tightened to apply a lateral compressive force to the wound or skin defect.

FIG. 3F shows a further closure apparatus adhered to the skin around the wound or skin defect and oriented transversely with respect to the first closure apparatus.

FIGS. 9A, 9B, and 9C show perspective, top, and schematic views, respectively, of a closure apparatus having a central open wound or incision area and tie elements arranged circumferentially in an end-to-end loop surrounding the central open wound or incision area, according to embodiments of the present disclosure.

FIGS. 12A and 12B show top views of a closure apparatus with and without a casting sheet, respectively, having a central open wound or incision area of 2 centimeters or less and tie elements arranged so as to flank the open wound or incision area, according to embodiments of the present disclosure.

FIGS. 13A and 13B show top views of a closure apparatus with and without a casting sheet, respectively, having a central open would or incision area of 5 centimeters or less, elastic elements, and tie elements arranged so as to flank the open wound or incision area, according to embodiments of the present disclosure.

DETAILED DESCRIPTION

Figure 1F:
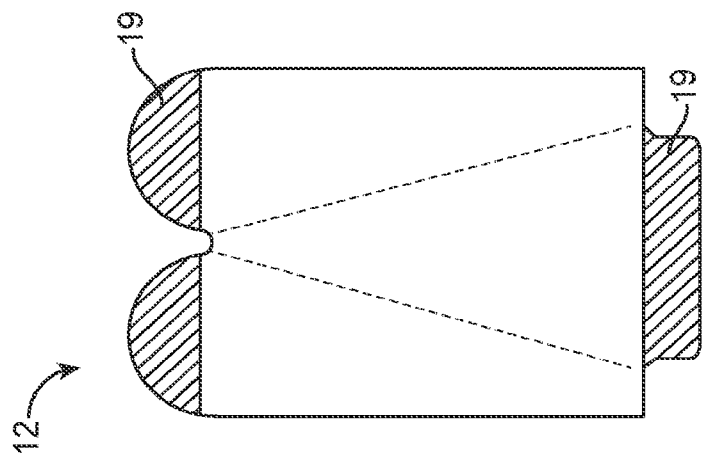
FIG. 1F shows a top view of the liner of the closure apparatus of FIG. 1A.
Figure 1E:
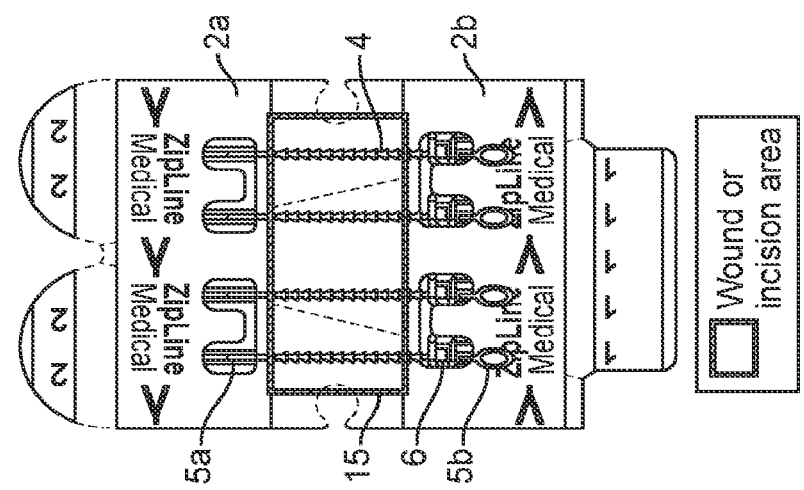
FIG. 1E shows another top view of the closure apparatus of FIG. 1A, including a wound or incision coverage area.
Figure 1D:
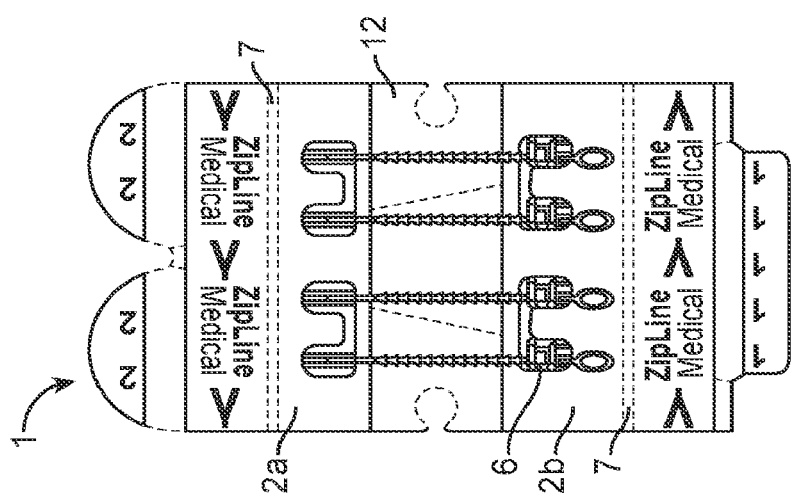
FIG. 1D shows another top view of the closure apparatus of FIG. 1A.

The following description may refer to the following terms which are further described as follows.

Arterial Skin Ulcer: Arterial skin ulcers account for up to 20% of all leg ulcers and develop when artery disease is present (sometimes in combination with venous disease). These ulcers tend to be extremely painful and are usually on the toes and feet, where poorly functioning arteries are least likely to circulate blood. These types of ulcers are typically caused by arteriosclerosis, which can lead to insufficient oxygenation of the skin and underlying tissues. This can kill the affected tissues and cause wounds.

Clean wound (Class I). A Class I clean wound is a surgically created wound, such as in an elective operating room (OR) case. Another condition to being a clean wound is that it does not involve the respiratory, gastrointestinal (GI), or GU (genitourinary) tracts. Laparoscopic surgeries, skin biopsies, and vascular surgeries are some examples.

Clean contaminated wound (Class II). A Class II contaminated wound involves normal tissue that is colonized by bacteria. Wounds which involve the respiratory, GI/GU tracts enter this category, as would wounds opened to remove pins or wires.

Closure by primary intention. Closure by primary intention is immediate closure of a wound, using sutures, staples, surgical tape, or tissue adhesive glue. Typically, such closure is used for a clean or contaminated wound after thorough cleansing and debridement.

Closure by secondary intention. Closure by secondary intention may allow a wound to heal naturally without any closure methods as above. This is the usual strategy for badly contaminated wounds (such as animal bites) and infected wounds.

Closure by tertiary intention: see Delayed primary closure.

Contaminated wound (Class III). A Class III contaminated wound contains foreign or infected matter—the most typical situation seen in emergency departments. Gross contamination is not required to meet this classification, any contact with a foreign object like a bullet, knife blade, or other sharp material may suffice.

Debridement. Debridement is the removal from tissue of all hyperkeratotic (thickened skin), infected, and nonviable including necrotic (dead) tissue, slough, foreign debris, and residual material from dressings.

Delayed primary closure. Delayed primary closure is a strategy of waiting to close a wound after about 48 hours, after it has proven not to have any signs of infection. This is also sometimes referred to as Closure by tertiary intention. This is a strategy typically employed for clean contaminated wounds and clean wounds that are older than 6 hours.

Diabetic Foot Ulcer. Diabetic foot ulcers, also known as neuropathic skin ulcers, occur in people who have little or no sensation in their feet due to diabetic nerve damage. These skin ulcers develop at pressure points on the foot, such as on the heel, the great toe, or other spots that rub on footwear. Treatment cost per ulcer episode varies widely according to ulcer depth, with an average cost estimated at $13,179. (Stockl K, Vanderplas A, Tafesse E, Chang E. Costs of lower-extremity ulcers among patients with diabetes. Diabetes Care 2004; 27:2129-2134.)

Fasciotomy. Fasciotomy is the standard treatment for acute compartment syndrome (ACS). Historically, fasciotomy incisions were either left open or immediately closed; however, the rates of infections and recurrent compartment syndrome were unacceptably high. In an attempt to improve outcomes, there is a plethora of different wound closure techniques published, which includes immediate closure, delayed primary closure, and ultimately utilizing a skin graft to fill the void Immediate or delayed primary wound closure may help decrease the infection rates and improve the cosmetic outcomes when compared with secondary closure and skin grafts. However, primary closure is not always possible, due to tissue edema. (Jauregui J, et. al. Fasciotomy closure techniques: A meta-analysis. 2017 Journal of Orthopedic Surgery, 25(1) 1-8.)

Infected (Class IV) wound. An infected (Class IV) wound is one with purulent drainage. These include wounds with a foreign object lodged in the wound like pieces of metal or other debris. This class can also include traumatic wounds from a dirty source where the treatment was delayed, infected surgical wounds, or any wound exposed to pus or fecal matter.

Negative Pressure Wound Therapy (NPWT). NPWT typically involves the application of a therapeutic dressing typically comprising a wound pad or sponge, an adhesive-backed occlusive sheet with a vacuum port, and a vacuum (i.e., negative pressure) generating device.

Off-loading. Off-loading is the relieving of the pressure from the ulcerated areas by having the patient wear special foot gear, a brace, specialized castings, or by using a wheelchair or crutches.

Pressure or Decubitus Ulcer: Pressure or decubitus ulcers or sores are localized areas of cellular necrosis resulting from prolonged pressure between any bony prominence and an external object such as a bed or wheelchair. The tissues are deprived of blood supply and eventually die. Areas frequently affected in older individuals include the heels (8%), greater trochanter (15%), sacrum (23%), and ischium (sit bones) (24%). They are common in bedridden individuals, especially the elderly. Older individuals with dementia are particularly prone.

Venous Skin Ulcers. Venous ulceration typically results from an elevated ambulatory venous pressure (venous hypertension). This frequently causes edema of the limb. External compression has been the mainstay to combat these problems. It is the most common ulcer, accounting for up to 80% of all leg ulcers. Chronic venous insufficiency can lead to venous stasis ulceration, which may occur as a result of previous deep venous thrombosis. The basic dysfunction is incompetent valves of the deep veins. The ulcers usually develop around the ankles, especially in the area of the medial malleoli. Loss of epidermis occurs, and portions of the dermal layer may also be involved, depending on the degree of venous stasis. A characteristic brownish coloration of the skin develops because of deposition of melanin and hemosiderin. When capillaries rupture, red blood cells are released and disintegrate, with subsequent release of hemosiderin.

The wound closure devices and their methods of use may be suitable for ulcers and irregularly shaped wounds, examples of which are described in Table 1 as follows.

stretching wound margins with tension sutures or commercially available devices may be problematic, as this technique can cause collateral skin damage, necrosis, and tear the skin margins during approximation of the opposing wound edges if excessive tension is applied. Additionally, commercial devices may be invasive, bulky, and may damage wound edges.

Delayed primary closure of surgical wounds or injuries may be used to address wound dehiscence, delayed closure after treatment of contaminated wounds (e.g., bullet and knife wounds), and incremental closure of fasciotomy. Currently, the inventors know of no dedicated products for this, which leaves treatment to incrementally adjusted tension sutures or healing by secondary intention.

Diabetic foot ulcers (DFU) occur in at least 15 percent of all people with diabetes mellitus and are the reason for approximately 20 percent of all hospitalizations of patients with diabetes. The most common causes of DFUs are diabetic peripheral neuropathy, existing foot deformity such as Charcot neuroarthropathy or partial foot amputation(s), biomechanical abnormalities, and/or peripheral vascular disease (PVD). Treatment focuses on healing by secondary intention and typically includes debridement, systemic antibiotics, off-loading of pressure from the area, creating and maintaining a clean, moist wound environment with spe-

TABLE 1

| Wound Type | Standard of Care | Gaps/Opportunities |
| --- | --- | --- |
| Diabetic Foot Ulcer (DFU) (The USA has a population of 18 million diabetics, with about 700,000 DFUs per year.) | Wound cleansing, aseptic surgical debridement, hydrogel dressing into the wound base covered by foam dressing. | Gentle, incremental external (i.e., topical) closure force, either standalone or in conjunction with other methods, may accelerate wound closure/healing by increasing perfusion to wound. |
| Venous Leg Ulcer (VLU) (The USA has occurrences of 2.2 million VLUs per year, and VLUs occur in 3.6% of those over 65 yrs old.) | 25% closure at 4 weeks, full closure @ 16 weeks. Extrinsic compression to minimize venous stasis, venous hypertension and edema. Newer methods include adding hydrocolloid dressings to compression. | Gentle, incremental external (i.e., topical) closure force, either standalone or in conjunction with compressive sleeves, may accelerate wound closure/healing by increasing perfusion to wound. |
| Dehisced Wound (Can be caused by mechanical force (fall) or infection.) | Clean, debride, treat infection; then, incrementally reclose with tension sutures or allow healing by secondary intention (granulation and reepithelialization). | Gentle, incremental external (i.e., topical) closure force may accelerate wound closure/healing and result in a superior cosmetic scar. |
| Fasciotomy | Success is defined as all wounds that could be closed without skin grafting, amputation, or death. The highest success rate was observed for dynamic dermatotraction and gradual suture approximation, whereas vacuum-assisted closure had the lowest complication rate. | Gentle, incremental external (i.e., topical) closure force may accelerate wound closure/healing and result in a superior cosmetic scar. |
| Pressure or Decubitus Ulcer | Treatment depends on stage of ulcer. Mainly, offload pressure, irrigation and dressings; severe ulcers require debridement, antibiotics and reconstruction with grafts or flaps. | Gentle, incremental external (i.e., topical) closure force, either standalone or in conjunction with other methods, may accelerate wound closure/healing by increasing perfusion to wound. |

The need for tension-reduction during wound closure is currently addressed by tension sutures or stretching devices designed to harness the viscoelastic properties of skin, applying controlled and evenly-distributed tension along the wound margins using incremental traction. The principle of cialized dressings and topically-applied medications. Newer approaches include negative pressure wound therapy (NPWT), which involves frequent specialized dressing changes and a vacuum generator device tethered to the dressing.

Surgical wound closure that is at particularly high risk of dehiscence may benefit from an adjunctive means of recruiting healthy tissue outside of the immediate incision site to help offload force and buffer the incision from any potential distraction force. Sternotomy is an example of this, where the result of wound dehiscence is often fatal.

The present disclosure includes improved wound closure devices, systems, and their methods of use.

FIGS. 1A-1E show a closure apparatus 1 according to embodiments of the present disclosure. The closure apparatus 1 may comprise two base panels 2a, 2b, coupled to one another by a plurality of reversibly adjustable lateral ties 4. Each base panel may comprise a bottom adhesive layer 13, a middle layer or main body 11, and a plurality of force distribution structures 10 coupled to the top of the middle layer 11. Each layer may be successively more rigid or less elastic from bottom to top, providing a vertical elasticity gradient, reducing adhesion loss and skin blistering when the skin upon which the closure apparatus is attached is moved.

The bottom adhesive layer 13 may be covered by one or more removable liners. For example, there may be a central liner removable from a tab on one side of the closure apparatus 1 and a pair of side liners 12 removable from tabs on the opposite side of the closure apparatus as shown in FIGS. 1A-1E, 3B, and 3C. Alternate liner configurations are also envisioned, for example, liners covering the bottom whole of the each of the base panels as shown in FIGS. 2A-2B, 4A-4B, 5A-5B, 6A-6B, and 7A-7B, or casting sheets covering the whole of the top each of the base panels and liners covering the bottom whole of each of the base panels as shown in FIGS. 11A-11B, 12A-12B, and 13A-13B. These liners 12 may be peeled from tabs at their longitudinal and/or lateral ends. As can be seen in FIGS. 11A, 12A, 13A, and 14A, each of the base panels can comprise a liner covering an adhesive layer and a casting sheet 16 which can removed from each of the top of the base panels. The casting sheet can aid in the placement of each of the base panels. For example, the casting sheet being adhered to each of the base panels can provide rigidity and stability to the base panels, making them easier to handle and place. After placement, the casting sheet may be removed. The bottom adhesive layer 13 may comprise a hydrocolloid adhesive. The lateral edges of the liners and/or liner tabs may be flattened as in FIGS. 4A-4B and 5A-5B or may be rounded as in FIGS. 6A-6B, 7A-7B, 11A, 12A, and 13A.

The middle layer or main body 11 of the base panels may lie over the bottom adhesive layer 13. The middle layer or main body 11 of the base panel may comprise a material such as a polymer material, such as polyurethane. In some embodiments, the main body of the base panel may comprise multiple, stepped layers as shown in FIGS. 5A-5B, FIGS. 7A-7B, and FIGS. 11A-11B. In some embodiments, the main body of the base panel 2a, 2b may comprise multiple perforations 7 as shown in FIGS. 11A-11B, 12A-12B, 13A-13B, and 14A. In some embodiments, the multiple perforations 7 are mirrored by perforations in the adhesive layer. The perforations 7 can provide lateral stress relief for acute strain on the device. The perforations 7 can help protect skin to which the adhesive is applied from acute lateral strain. For example, the perforations 7 can accommodate the underlying skin stretching and contracting in various direction by facilitating the stretching and contracting of the base panels along with the skin, thereby reducing adhesion loss and/or lowering the risk of blistering from skin adhesion that may otherwise be too strong.

Force distribution structures may be coupled to the top surfaces of the base panels, and the ends of the lateral ties 4 may be coupled to the force distribution structures to distribute the forces from the attachment of the wound closure apparatus to the skin as concentrated by the attachment points of the lateral ties. For example, the lateral ties may have fixed ends 5a at one base panel 2a and adjustably coupled ends 5b at the other base panel 2b with locks 6 as can be seen in FIGS. 1A-1E. The lateral ties may be coupled to the base panels 2a, 2b, at a predetermined adjustable distance to provide a predetermined lateral gap 8 between the inner lateral edges of the base panels, as can be seen in FIGS. 1A-1B. The separation distance between the base panels may be large enough to encompass the most common ulcers. A suite of closure apparatuses, each with different sized lateral gaps 8 and separation distances, may be provided. FIGS. 2A, 11A, 12A, and 13A show a top view of a wide closure apparatus and FIGS. 2B, 11B, 12B, and 13B show the wide closure apparatus with the release liner removed.

Alternatively or in combination, a suite of closure apparatus 1 with different length base panels may be provided. The separation distances may be enlarged or reduced by adjusting the adjustable end of the lateral ties 5b, and the separation distance may be adjusted to be larger or smaller at different lateral ties. The separation distance may start, for example, at 10 mm or greater, 20 mm or greater, 30 mm or greater, 40 mm or greater, or 50 mm or greater. The closure apparatus may be configured to encompass and treat an ulcer or skin defect with a minor axis of at most 50 mm, 40 mm, 30 mm, at most 20 mm, or at most 10 mm, for example. The lateral ties 4 will typically be more rigid than the middle layer or main body of the base panels and may comprise a material like nylon.

Figure 8B:
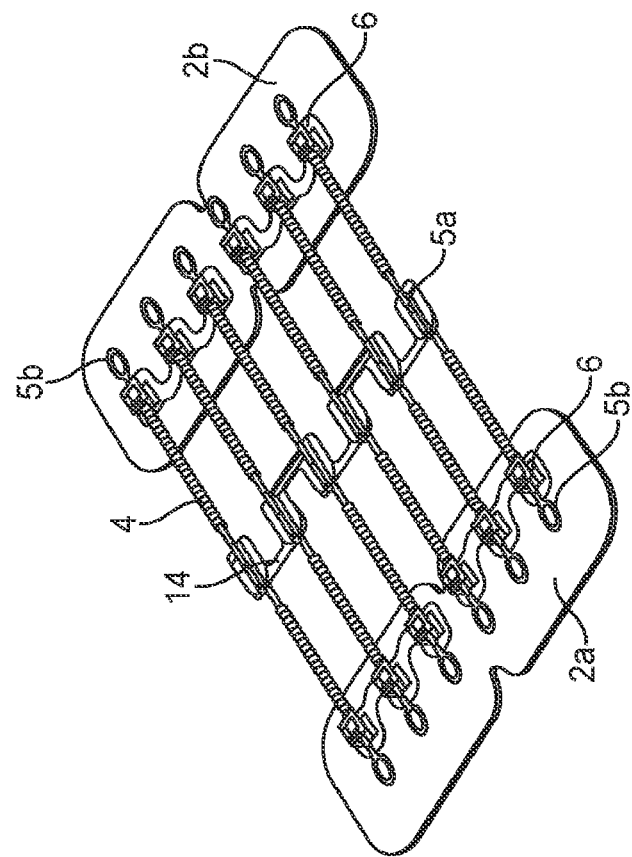
FIGS. 8A and 8B show top and perspective views, respectively, of a closure apparatus having lateral ties with elastic or spring components, according to embodiments of the present disclosure.
Figure 8A:
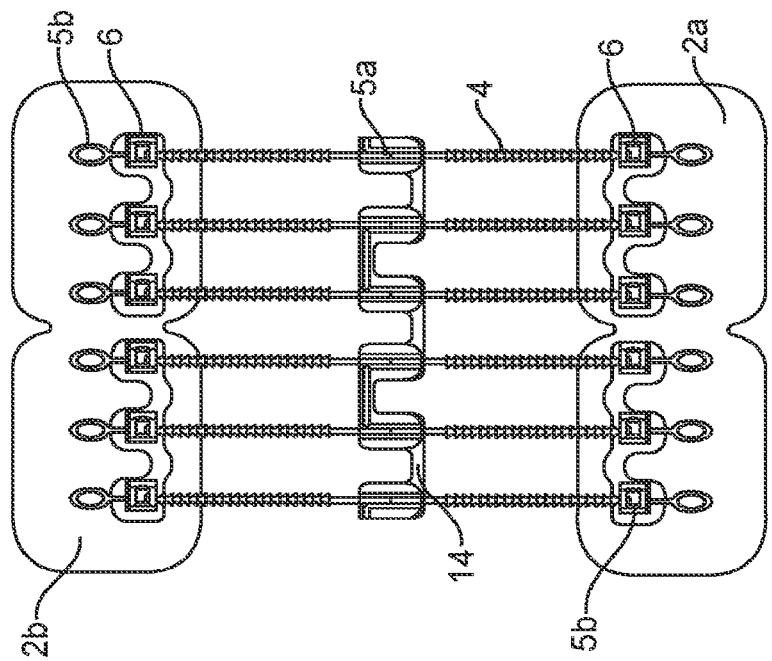

In some embodiments, particularly those with larger separation distances as shown in FIGS. 8A, 8B, 13A and 13B, the lateral ties may be provided with one or more spring or elastic components along their lengths and/or be adjustable from either base. The spring or elastic component(s) 14 may provide dimensional stability to the lateral ties 4, allowing some movement of the lateral ties 4 relative to one another in directions transverse to the length of the lateral ties 4 as well as along their lengths while restricting too much movement. As shown in FIGS. 8A-8B and 13A-13B, tie elements may have their fixed ends coupled to an elastic component 14 positioned over the open wound or incision 15, while the adjustable ends 5b are coupled to force distribution structures 3 coupled to the upper surface of the middle, main layer 11 on the flanking base structures 2a, 2b. As shown in FIGS. 8A and 8B, the spring or elastic component(s) 14 may be in the form of a length of rigid material having a serpentine configuration. As shown in FIGS. 13A and 13B, the spring or elastic component(s) 14 may be in the form of separate units of rigid material between groupings of two lateral ties. The material may be similar or the same as that of the force distribution structure elements 3 and/or lateral ties 4, such as nylon.

The closure apparatus may share many features in common with the closure apparatuses described in U.S. Patent Applications: U.S. patent application Ser. No. 13/286,757 (now U.S. Pat. No. 8,323,313), Ser. Nos. 13/665,160, 14/180,524 (U.S. Pat. No. 9,050,086), Ser. Nos. 14/180,564, 14/625,366 (U.S. Pat. No. 9,642,621), Ser. No. 15/081,526 (U.S. Pat. No. 9,474,529), Ser. No. 15/081,550 (U.S. Pat. No. 9,554,799), Ser. No. 15/081,595 (U.S. Pat. No. 9,642,622), Ser. No. 15/096,083 (U.S. Pat. No. 9,554,800), Ser. No. 15/130,149 (U.S. Pat. No. 9,561,034), and Ser. No.

15/369,293, and PCT Application Nos. PCT/US2015/028066, PCT/US2016/028297, and PCT/US2017/028537, which are incorporated herein by reference in its entirety.

Figure 3A:
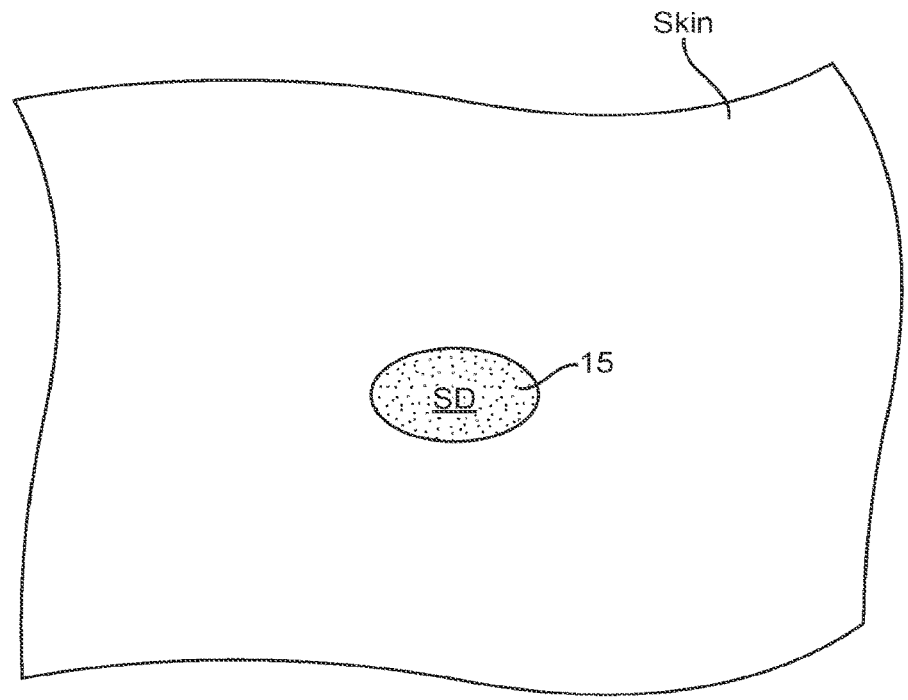
FIGS. 3A-3F shows a method of applying a closure apparatus to a wound or skin defect, according to embodiments of the present disclosure.
Figure 3B:
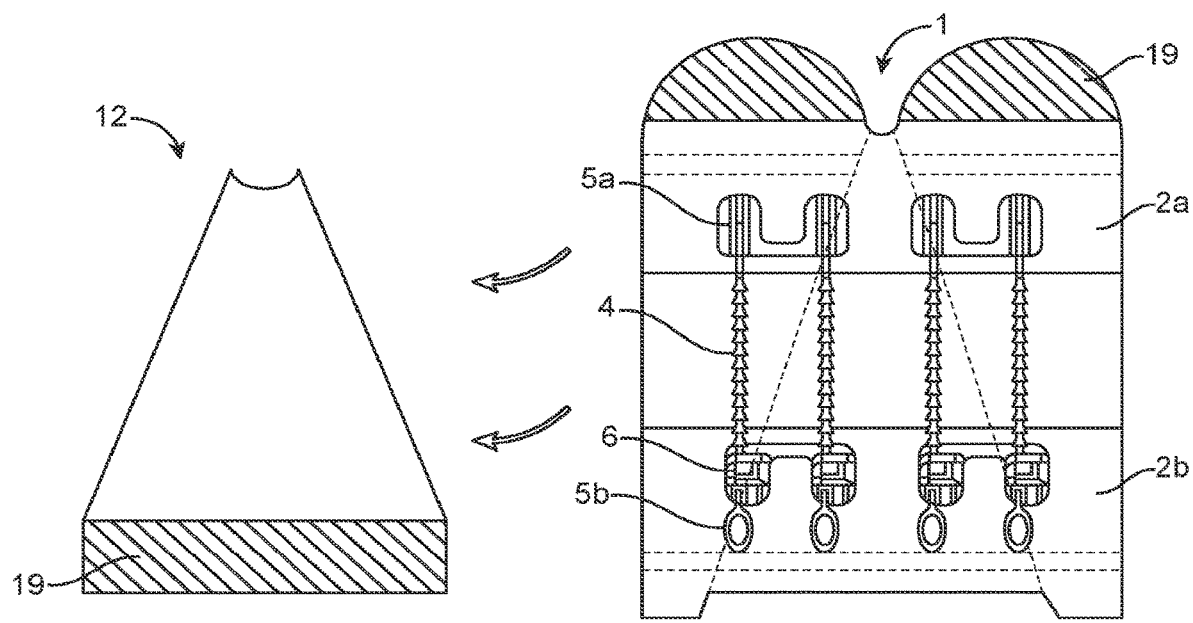
Figure 3C:
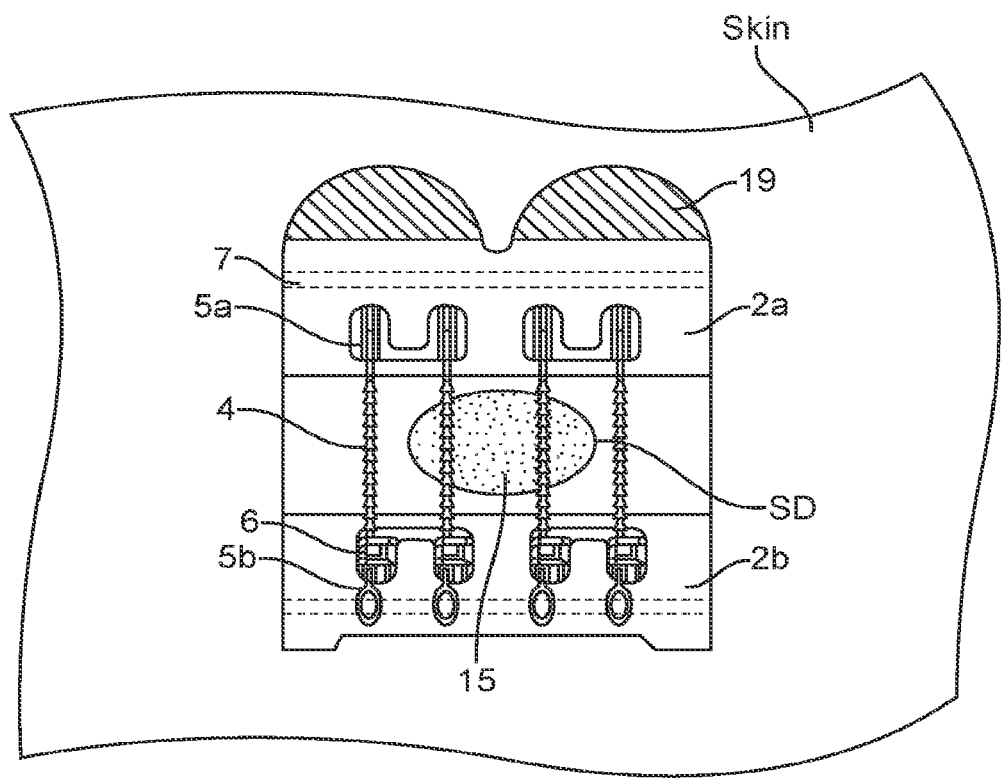
Figure 3D:
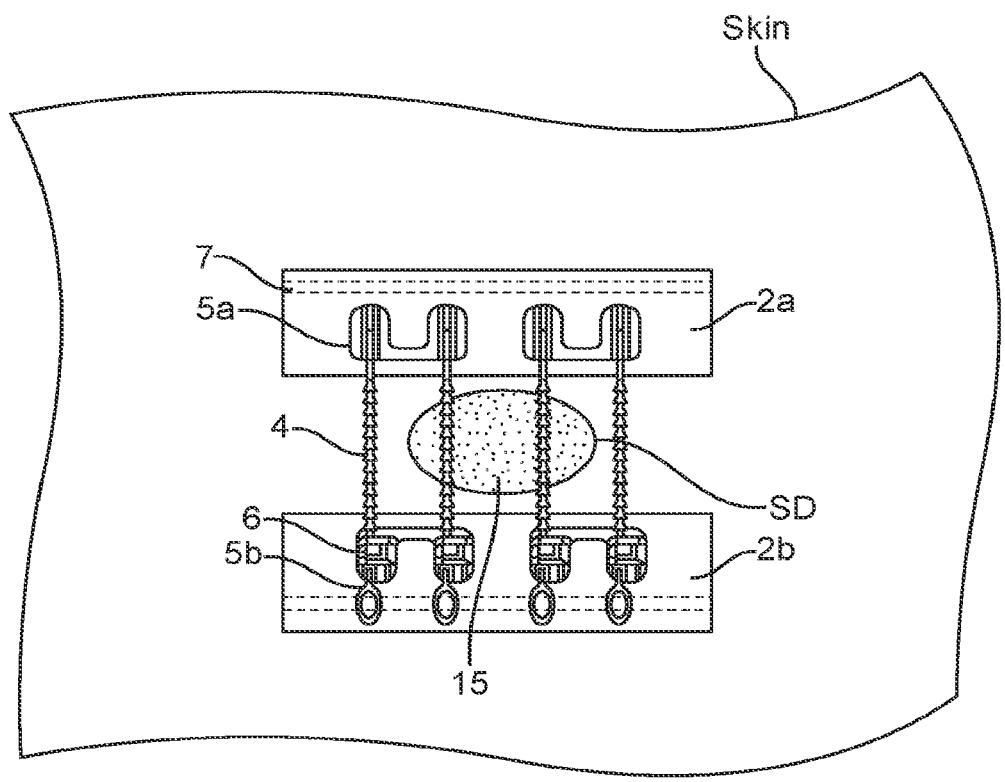
Figure 3E:
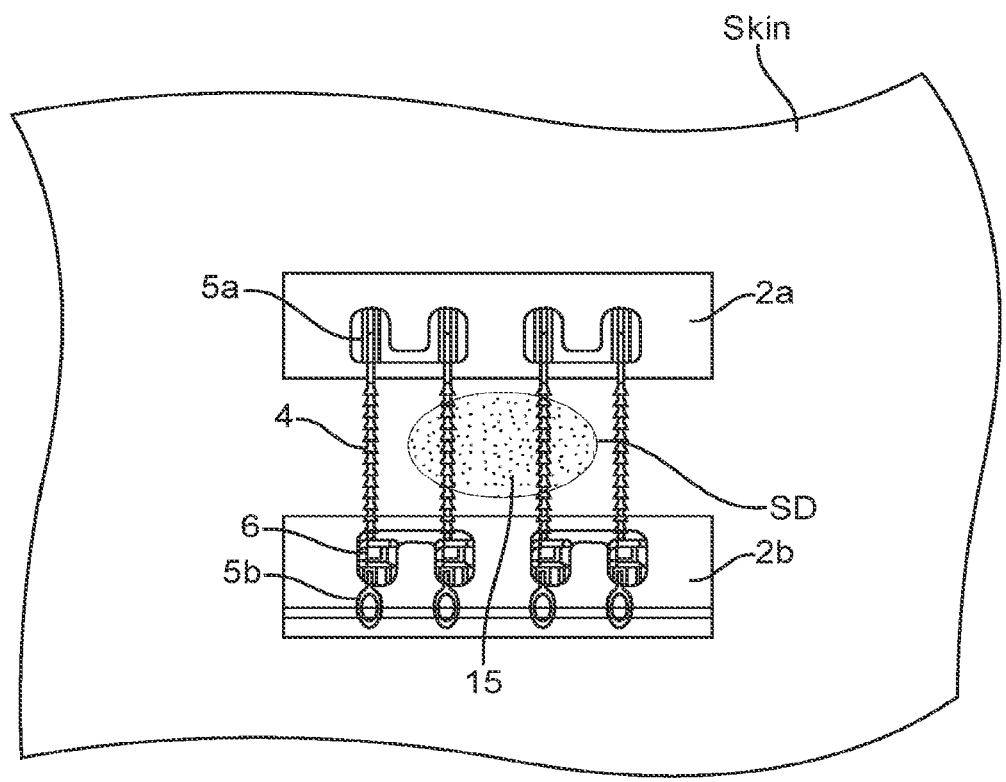
Figure 3F:
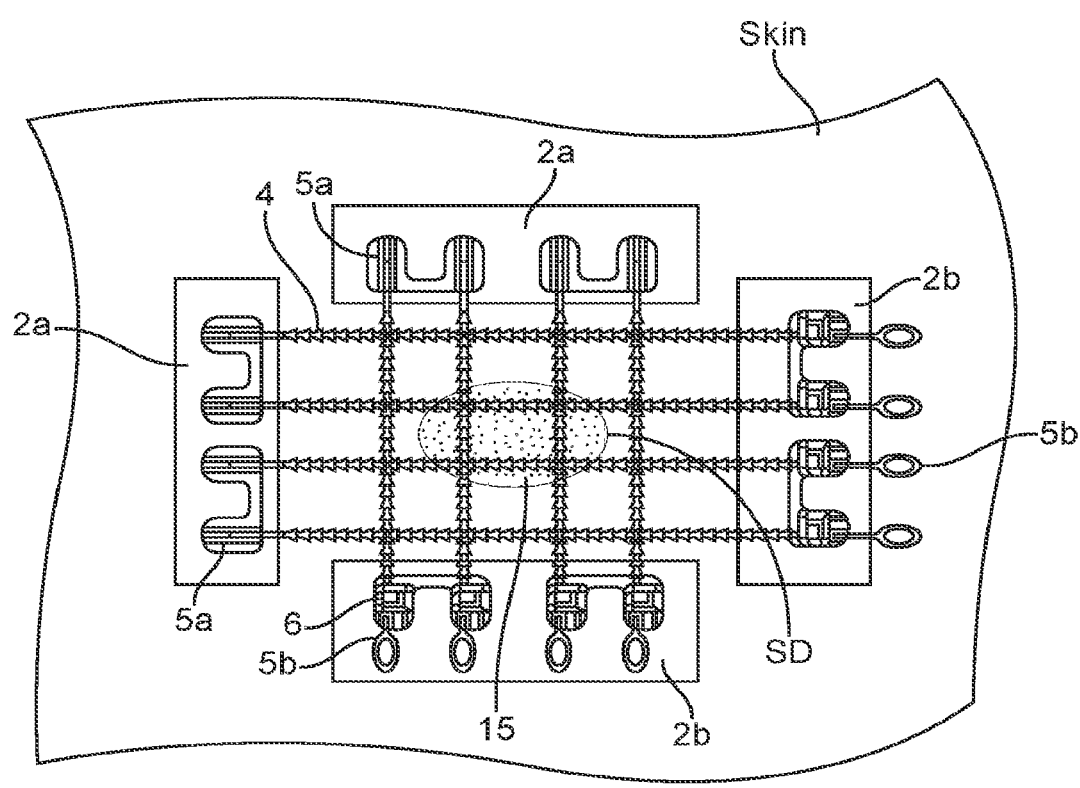
Figure 4A:
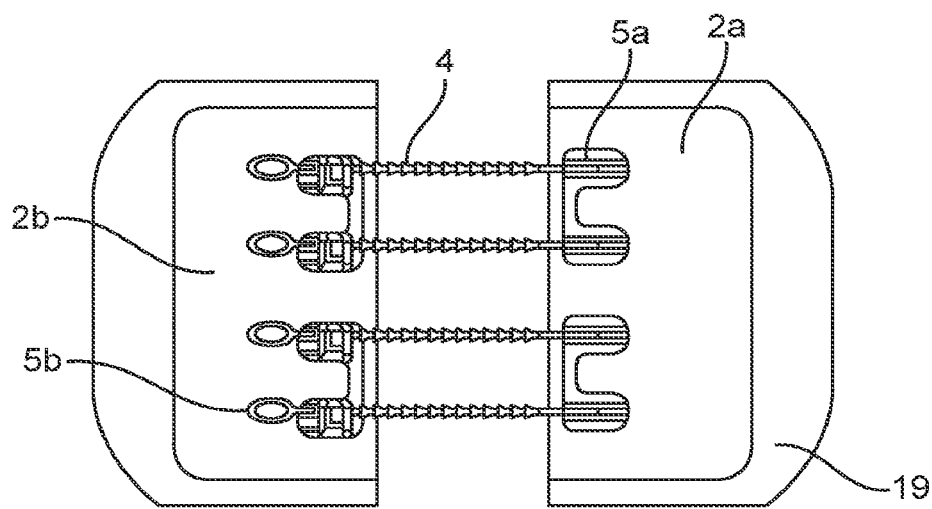
FIGS. 4A and 4B show top and perspective views, respectively, of a closure apparatus with flattened lateral edges, according to embodiments of the present disclosure.
Figure 4B:
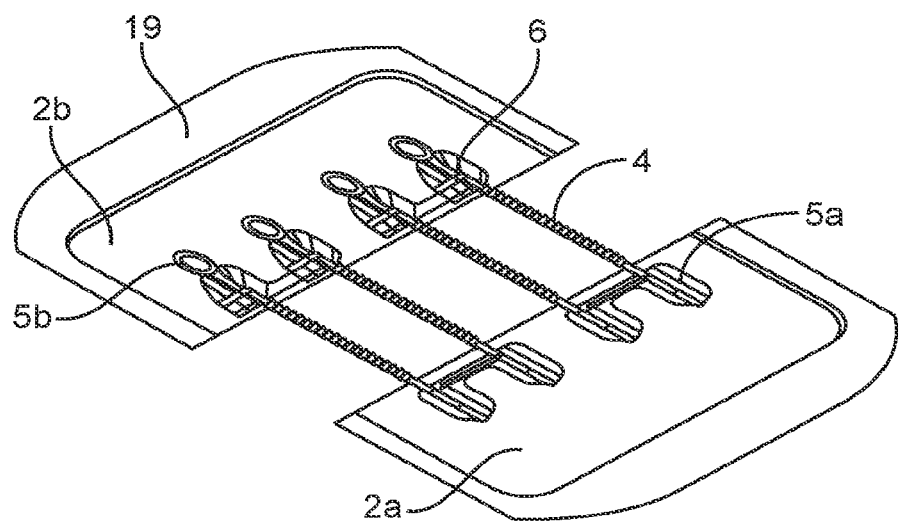
Figure 5A:
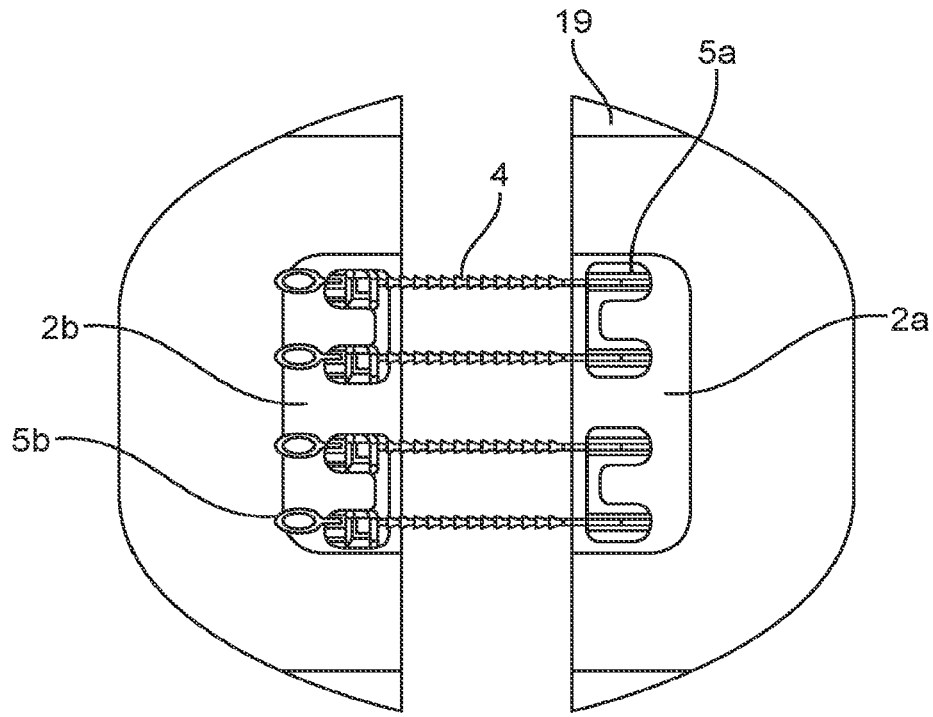
FIGS. 5A and 5B show top and perspective views, respectively, of a closure apparatus with flattened lateral edges and multi-layered main panels, according to embodiments of the present disclosure.
Figure 5B:
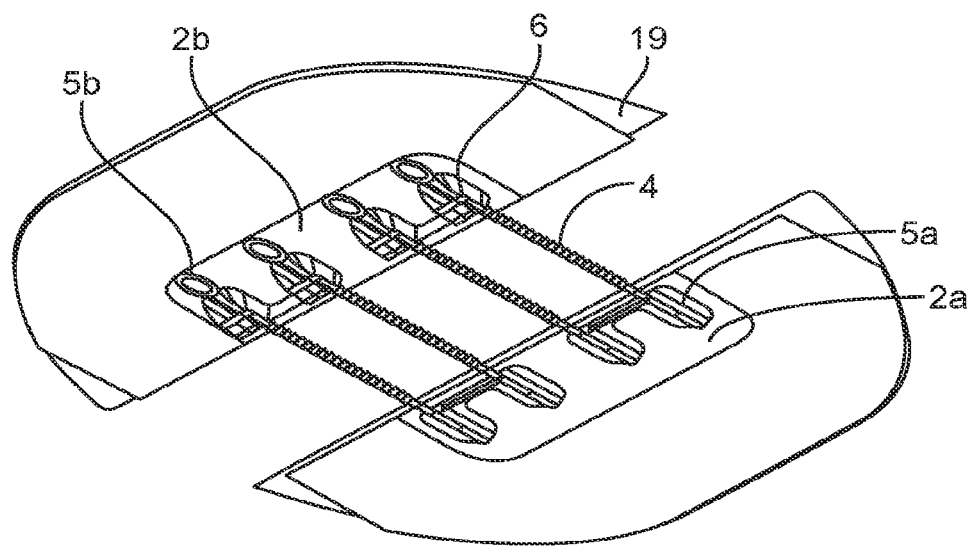
Figure 6A:
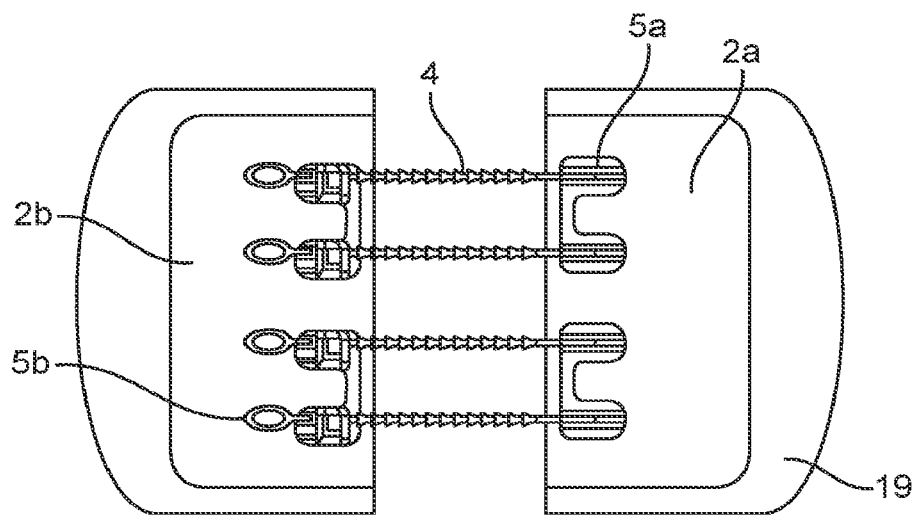
FIGS. 6A and 6B show top and perspective views, respectively, of a closure apparatus with rounded lateral edges, according to embodiments of the present disclosure.
Figure 6B:
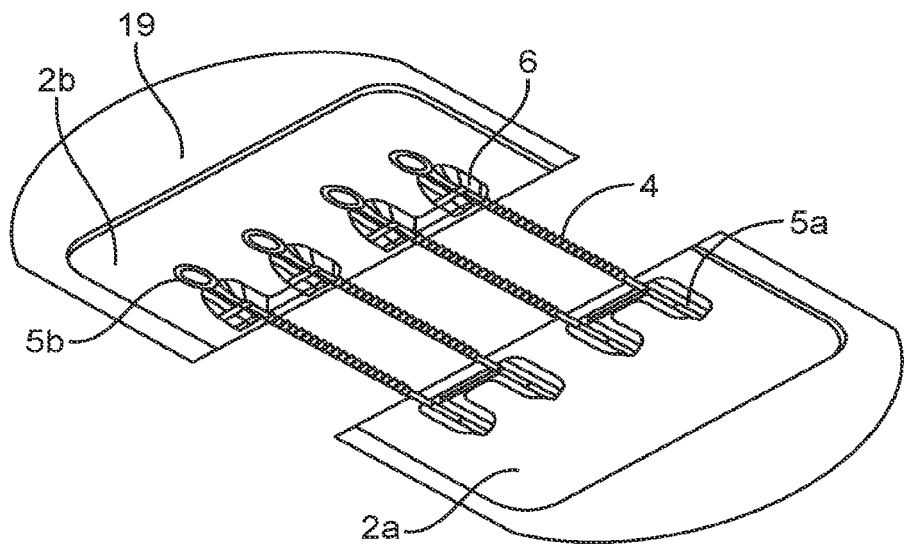
Figure 7A:
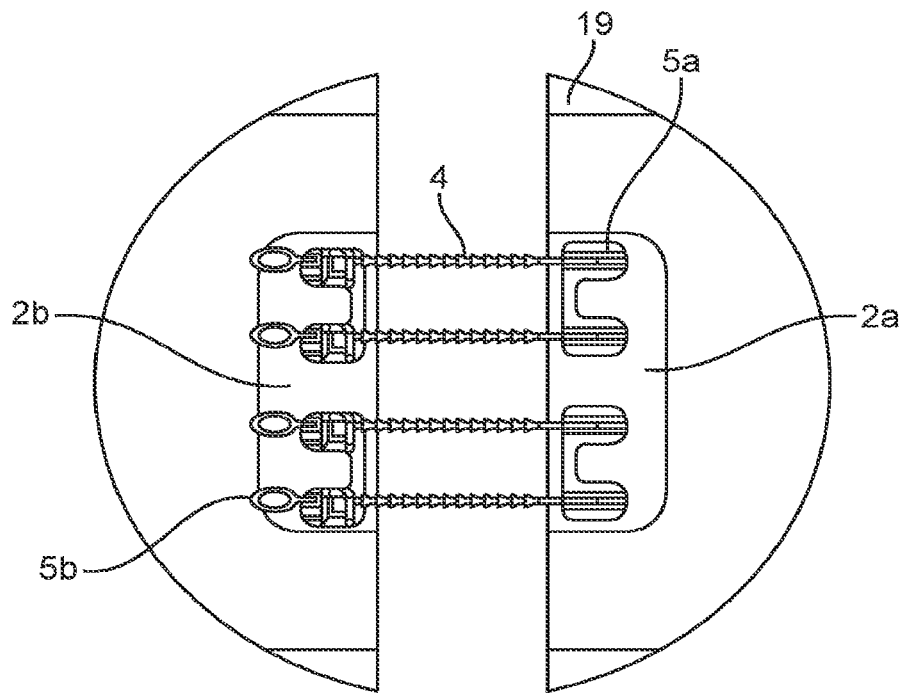
FIGS. 7A and 7B show top and perspective views, respectively, of a closure apparatus with rounded lateral edges and multi-layered main panels, according to embodiments of the present disclosure.
Figure 7B:
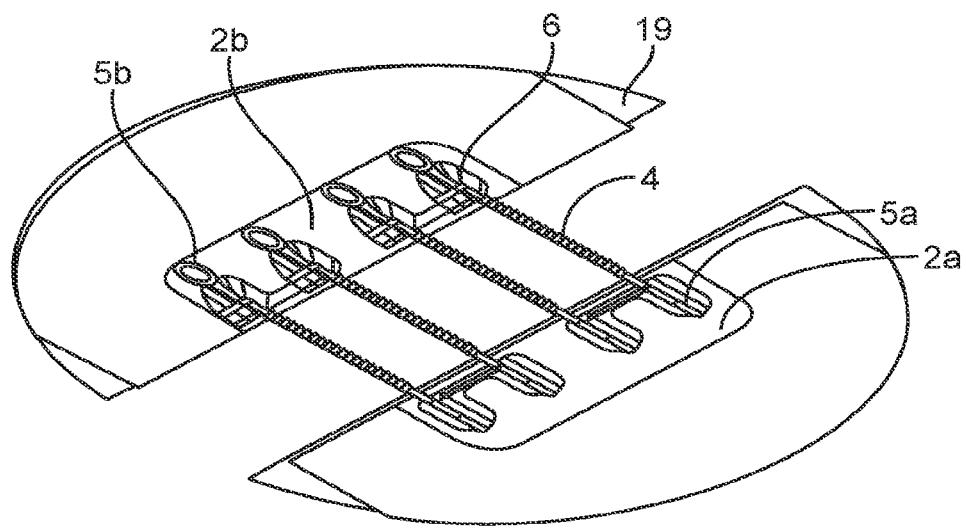

FIGS. 3A-3F shows a method of applying a closure apparatus to a wound 15 or skin defect SD. The ulcer or skin defect may be a diabetic foot ulcer, a venous leg ulcer, an arterial ulcer, a dehisced wound, a dehisced infection, a fasciotomy, a pressure or decubitus ulcer, or a biopsy incision. As shown in FIG. 3B, the central liner 12 may be removed by peeling the central liner away from the rest of the closure apparatus with the tab 19 of the central liner. With the adhesive layers of the closure apparatus exposed, the closure apparatus may be positioned over the wound or skin defect SD to encompass the wound 15 or skin defect between the inner lateral edges of the base panels 2a, 2b, and the closure apparatus may be pressed against the skin adjacent the wound or skin defect SD to adhere the closure apparatus 1 thereto as shown in FIG. 3C. Subsequently, the two liners laterally adjacent the central liner may be peeled away to expose the rest of the adhesive layers 13, and the closure apparatus 1 may be pressed against the skin to fully adhere the closure apparatus thereto as shown in FIG. 3D. Once adhered, the lateral ties 4 may be adjusted and tightened to apply a lateral compressive force to the wound or skin defect as shown in FIG. 3E. In some cases, an additional wound closure apparatus may be similarly applied over the wound or skin closure SD as shown in FIG. 3F. The additional wound closure apparatus may be placed in an orientation transverse to the first wound closure apparatus as shown in FIG. 3F. Also, in some cases, a liquid glue, an anti-microbial agent, an antibacterial agent, and/or other therapeutic agent may be applied to the wound or skin defect SD before, after, or during application of the one or more closure apparatuses.

Form factors for closure devices other than two parallel base panels are also disclosed. Closure devices according to embodiments of the present disclosure may be in the form of a patch having a central wound or incision treatment aperture 20 that is open, as shown, for example, by FIGS. 9A-9C, 10A-10B, and 14A. As shown in FIGS. 9A-9C, 10A-10C, and 14A, the closed shape closure device may be generally circular, ovoid, elliptical, or hexagonal, but may also be provided in other geometries such as a triangular, rectangular, square, pentagonal, or in the shape of another polygon. The outer peripheral edge of the closed shape closure device may be scalloped or sinusoidal in shape to provide flexibility for the closure device in response to lateral forces adjacent the closure device when adhered, thereby reducing the chance of skin blistering and adhesion loss.

As shown in FIGS. 9A-9C, the closed shape closure device may comprise a single base 9 with an adhesive bottom layer 13 and a middle, main layer 11 similar to the adhesive bottom layers 13 and base panel main body layer 11 described above. A plurality of tie elements, similar to the lateral tie elements 4 described above, may be attached to force distribution elements 10 fixedly coupled to the upper surface of the middle, main layer 11. The tie elements may be arranged circumferentially in an end-to-end loop surrounding the central open wound or incision area 22. Each tie element may comprise a fixed end 5a fixedly attached to its respective force distribution element and an adjustable end 5b adjustably attached to its respective force distribution element. Fixed ends of each tie element may be immediately adjacent the adjustable ends of the next tie element over. As shown in FIGS. 9B and 9C, the tie elements may be reversibly tightened to shrink the central open wound or incision area and provide compressive force to the area.

Figure 10B:
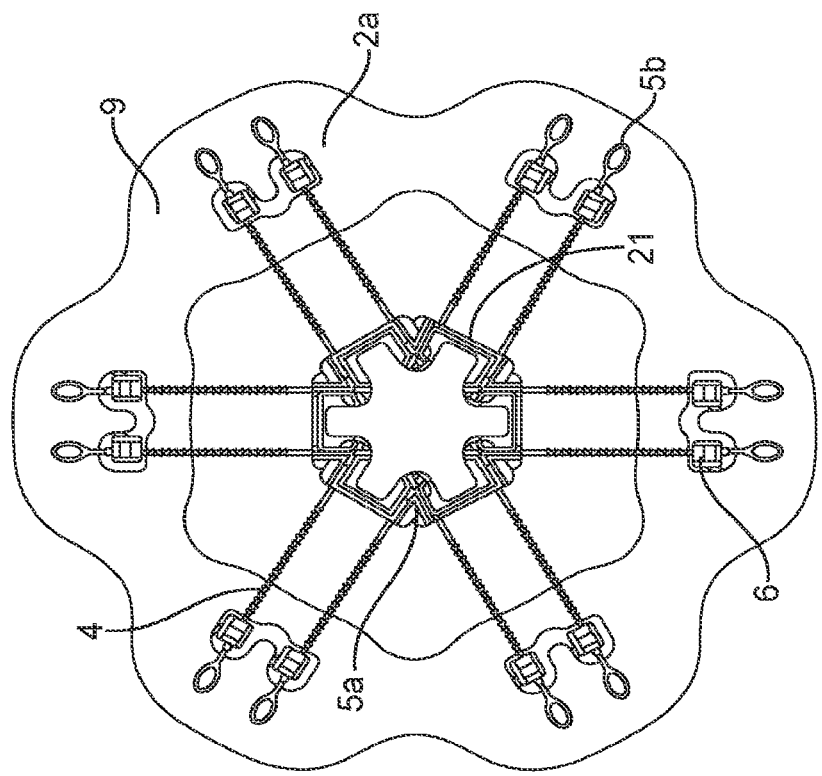
FIGS. 10A and 10B show perspective and top views, respectively, of a closure apparatus having a central open wound or incision area and tie elements arranged radially about the central open wound or incision area, according to embodiments of the present disclosure.
Figure 10A:
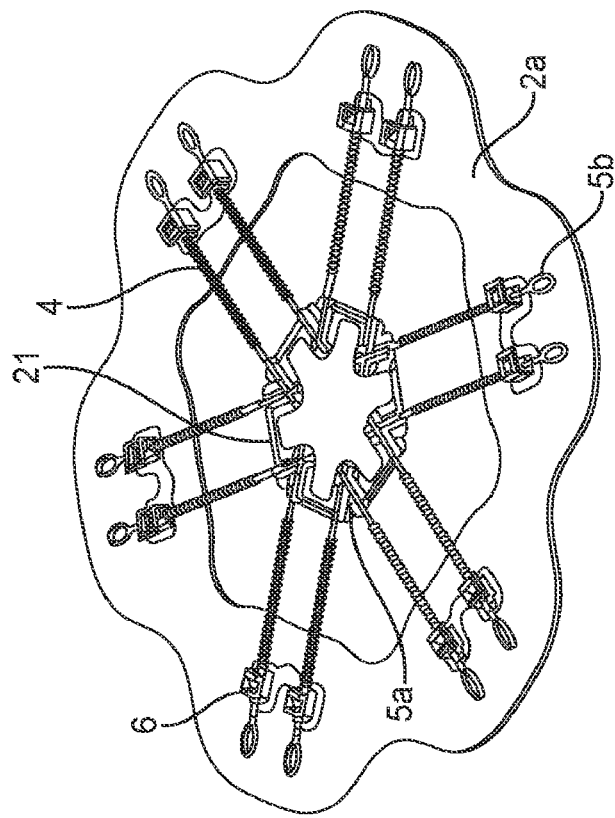
Figures 11A, 11B:
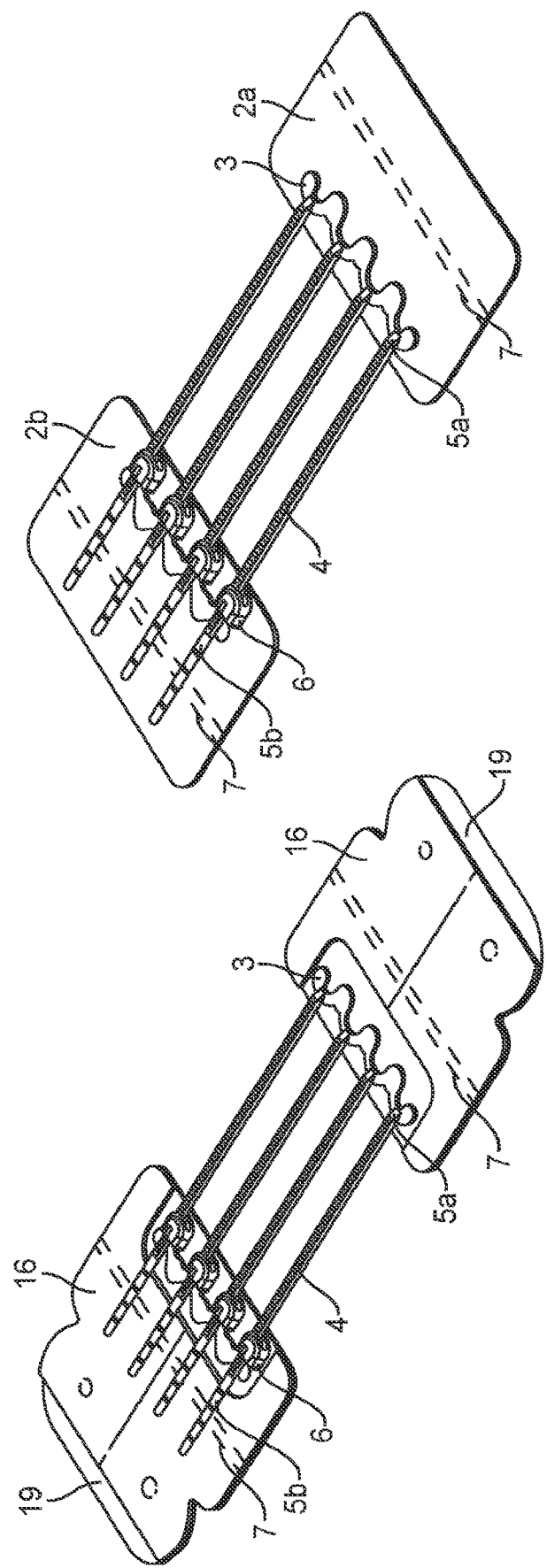
FIGS. 11A and 11B show top views of a closure apparatus with and without a casting sheet, respectively, having a central open wound or incision area of 5 centimeters or less and tie elements arranged so as to flank the open wound or incision area, according to embodiments of the present disclosure.
Figure 14B:
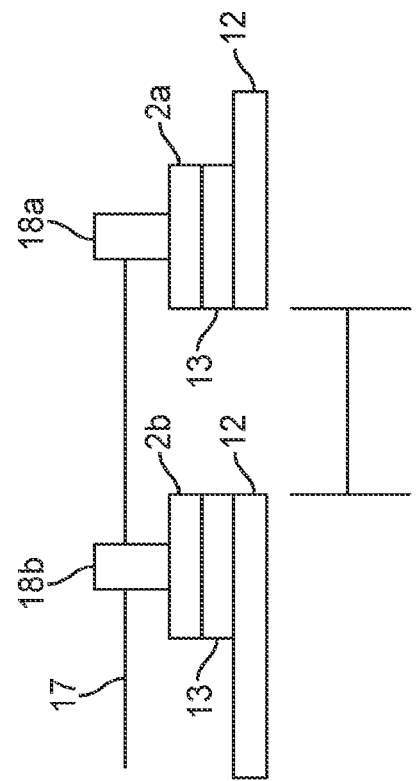
FIGS. 14A and 14B show a top and side view, respectively, of a closure apparatus having a central open wound or incision area, a single closure element, and opposing curved bases arranged so as to flank the open wound or incision area, according to embodiments of the present disclosure.
Figure 14A:
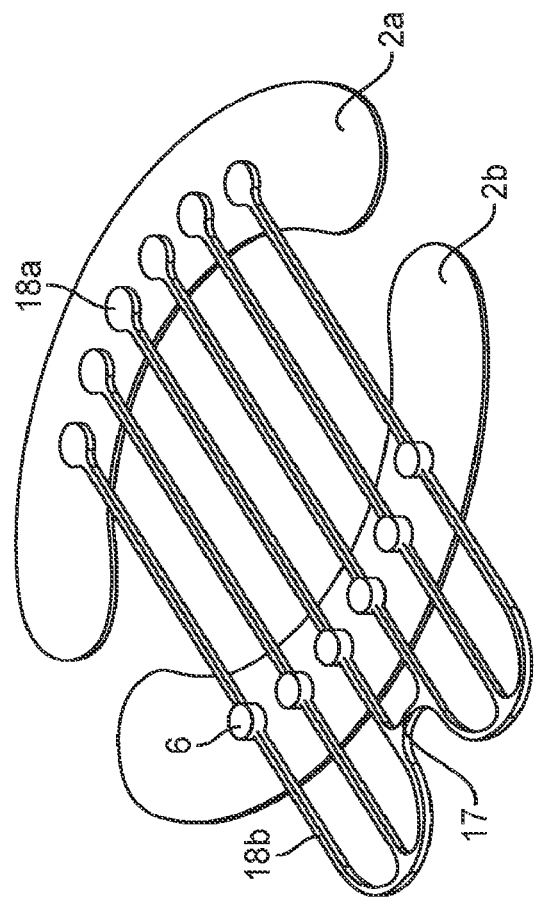

As shown in FIGS. 10A-10B and 14A, other arrangements of tie elements for the closed shape closure device are also provided. As shown in FIGS. 10A-10B, tie elements may have their fixed ends coupled to a central hub structure 21 positioned within the central open wound or incision treatment aperture 20, while the adjustable ends 5b are coupled to force distribution structures 3 coupled to the upper surface of the middle, main layer 11 closer to the periphery of the closure device. This arrangement can leave the center of the hub structure 21 open and free of any interfering structure such as the free ends of the tie elements. In other embodiments, the adjustable ends 5b are coupled to the central hub structure 21 and excess material can be simply cut or clipped away once adjusted as desired. The central hub structure 21 may be made of the same material as the tie elements 4 and force distribution structures 10, such as nylon. As show in FIG. 14A, tie elements may be a single closure element 17 with a fixed end 18a coupled to force distribution structures 10 coupled to the upper surface of a first base structure 2a opposite a second base structure 2b that is coupled to the adjustable end 18b of the closure element. The base structures can be curved to form an oval shape, a circular shape, a hexagonal shape, a square shape, etc.

One or more of the components of the incision closure appliances or incision closure appliance assemblies disclosed herein, including one or more of the various base assemblies, base panels, force distribution structures, axial supports, lateral supports, closure components, tie assemblies, tie elements, straps, locks, adhesive layers, adhesive layers, etc., may be comprised of, be coated with, or otherwise incorporate one or more of an antifungal, antibacterial, antimicrobial, antiseptic, or medicated material. For example, such materials may be incorporated into the hydrocolloid adhesive layer, as another layer or coating between the skin and the adhesive layer (covering at least a portion of the adhesive layer), incorporated into the base assembly cover or at least its adhesive layer, etc. One or more wells, grooves, openings, pores, or similar structures may be provided on the device or apparatus components to facilitate such incorporation. In many embodiments, such materials may comprise one or more of silver, iodide, zinc, chlorine, copper, or natural materials such as tea tree oil as the active agent. Examples of such antifungal, antibacterial, antimicrobial, antiseptic, or medicated materials include, but are not limited to, the Acticoat™ family of materials available from Smith & Nephew plc of the U.K., the Acticoat™ Moisture Control family of materials available from Smith & Nephew plc of the U.K., the Contreet™ Foam family of materials available from Coloplast A/S of Denmark, the UrgoCell™ Silver family of materials available from Urgo Limited of the U.K. (a subsidiary of Laboratoires URGO of France), the Contreet™ Hydrocolloid family of materials available from Smith & Nephew plc of the U.K., the Aquacel™ Ag family of materials available from ConvaTec Inc. of Skillman, N.J., the Silvercel™ family of materials available from Kinetic Concepts, Inc. of San Antonio, Tex., Actisorb™ Silver 220 available from Kinetic Concepts, Inc. of San Antonio, Tex., the Urgotul™ SSD family of materials available from Urgo Limited of the U.K. (a subsidiary of Laboratoires URGO of France), the Inadine™ family of materials available from Kinetic Concepts, Inc. of San Antonio, Tex., the Iodoflex™ family of materials available from Smith & Nephew plc of the U.K., the Sorbsan Silver™ family of materials available from Aspen Medical Europe Ltd. of the U.K., the Polymem Silver™ family of materials available from Ferris Mfg. Corp. of Burr Ridge, Ill., the Promogram™ family of materials available from Kinetic Concepts, Inc. of San Antonio, Tex., the Promogram Prisma™ family of materials available from Kinetic Concepts, Inc. of San Antonio, Tex., and the Arglaes™ family of materials available from Medline Industries, Inc. of Mundelein, Ill. Components of the closure devices described herein may be comprised of, be coated with, or otherwise incorporate one or more of an antifungal, antibacterial, antimicrobial, antiseptic, or medicated material, including but not limited to one or more of the materials listed above.

In many embodiments, topical medicinal agents are incorporated directly into the wound closure appliances described herein. Because a wound closure device is often applied in close proximity to a wound or incision in need of medicinal protection, the incorporation of such medicines directly into the closure device may be beneficial. In wounds at risk of infection, incorporation of anti-microbial agents may be beneficial, for example. Anti-microbial agents may include antibiotic medicines as well as antiseptic metal ions and associated compounds which may include silver, iodine, copper, and chlorine, or natural materials such as tea tree oil. In wounds prone to fungus, medicinal agents such as zinc may be warranted, for example. Combinations of any of these agents may also be of benefit and thus may be incorporated into wound closure appliances.

Topical medicinal agents may be incorporated into the closure devices in a way to give the closure devices the ability to wick exudate away from the wound (e.g., to direct unwanted organisms away from the wound and/or prevent skin maceration), while keeping the wound sufficiently hydrated for improved healing.

According to further aspects of the present disclosure, after assembly of a closure device (such as closure apparatus 1) a coating can be applied to the outer surface to prevent adhesion to the wound dressing. An exemplary coating may utilize a non-stick fluoropolymer coating applied and cured to the device 1, typically with a process that does not require temperatures exceeding 60° C. for 5 min, and more preferably under 45° C. for any period of time. The adherence of the coating with the polyurethane film of the wound closure device may be most desired, though protection of all external surfaces may be desirable as well. The fluoropolymer film thickness may range from 0.25 to 5.0 microns, preferably about 1-3 microns. Coating would typically take place with release liners or other suitable material in contact with the skin adhesive surface to prevent contamination of the skin adhesive with the coating. Such a coating would typically be applied as part of the manufacturing process such that no additional coating is required to be applied by the user. However, in other embodiments, just before dressing application, the user may instead apply a preferably sterile oil-based liquid or gel to the outside of the closure apparatus 1 to prevent adhesion. Examples include petrolatum and silicone oil.

Other coatings that do not require cure temperatures that can damage the device adhesives (typically above 60° C.) may be applied. These may include silicone compounds or oils (cured to the material or uncured), parylene, and other coatings well-known in the art. The coating may preferably remain bound to the closure device upon removal of the dressing, though could also act by deadening the applied adhesive, and/or acting as a sacrificial layer that is pulled up with the dressing instead of the underlying device. Sacrificial coatings may be thicker, more in the range of 0.0005"–0.010".

While preferable to apply to the entire finished device, the coating could be applied to selective regions of the device by masking areas to not be coated. This may be useful if coating is incorporated into an intermediary process where component bonding must be subsequently performed to non-coated regions of the device, or if coating of other components (e.g., the locks and straps) results in undesirable low friction (e.g., straps don't stay engaged in locks or strap slips out of user's hands). In other cases, the coating may be on a material that is applied separately to the device (e.g., a strip of polyurethane film). This may be useful if the coating process requires an elevated temperature or use of solvents that are incompatible with the rest of the device.

In other embodiments, the coating material may have an antimicrobial compound incorporated into the coating. The coatings described above are preferably conformal to the device surfaces and remains adhered to the closure device at least until the wound dressing is applied. The coatings described also offer minimal resistance to closure device stretch (up to 50%) and themselves do not loose protective effects while the dressing is worn against the closure device.

In other embodiments, an anti-microbial and/or a topical medicinal agent may be applied to the wound or defect prior to, during, or after application of the device to the skin. The anti-microbial and/or topical medicinal agent may be any of those mentioned herein.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

What is claimed is:

1. A device for treating an ulcer or skin defect, comprising:
    a first panel having a first adhesive bottom layer for adhering to skin on a first side of an ulcer or skin defect;
    a second panel having a second adhesive bottom layer for adhering to skin on a second side of the ulcer or skin defect;
    a plurality of lateral ties coupling the first panel and the second panel to one another;
    one or more liners coupled to the first adhesive bottom layer and the second adhesive bottom layer;
    a first casting sheet covering a top surface of the first panel, wherein the first casting sheet extends outwardly from a lateral end of the first panel; and
    a second casting sheet covering a top surface of the second panel, wherein the second casting sheet extends outwardly from a lateral end of the second panel,
    wherein the one or more liners comprise tabs extend outwardly from ends of the first casting sheet and the second casting sheet to assist with peeling the one or more liners from the first panel and the second panel prior to adhering the first adhesive bottom layer to the first side of the ulcer or skin defect and adhering the second adhesive bottom layer to the second side of the ulcer or skin defect,
    wherein the first casting sheet is removable from the top surface of the first panel after adhering the first adhesive bottom layer to the first side of the ulcer or skin defect, and wherein the second casting sheet is removable from the top surface of the second panel after adhering the second adhesive bottom layer to the second side of the ulcer or skin defect.

2. The device of claim 1, wherein the plurality of lateral ties are configured to maintain a separation distance of at least 10 mm between inside lateral edges of the first panel and the second panel.

3. The device of claim 1, wherein the one or more liners comprises a first liner removably coupled to the first adhesive bottom layer of the first panel and a second liner removably coupled to the second adhesive bottom layer of the second panel.

4. The device of claim 1, wherein the first and second adhesive bottom layers of the first and second panels comprise a hydrocolloid adhesive.

5. The device of claim 4, wherein the first and second panels comprise base layers positioned over the hydrocolloid adhesive, the base layers being more rigid than the hydrocolloid adhesive, wherein, the first and second panels each further comprise one or more force distribution structures coupled to the base layers, the force distribution structures being more rigid than the base layers.

6. The device of claim 5, wherein the first casting sheet and the second casting sheet do not cover the one or more force distribution structures.

7. The device of claim 5, wherein the plurality of lateral ties each have a fixed end coupled to the one or more force distribution structures of the first panel and an adjustable end coupled to the one or more force distribution structures of the second panel,
wherein the plurality of lateral ties comprise one or more elastic components along a length of the plurality of lateral ties between the fixed ends and the adjustable ends, and
wherein each of the one or more elastic components couples two of the plurality of lateral ties to each other.

8. The device of claim 1, wherein the plurality of lateral ties are at least partially elastic.

9. The device of claim 8, wherein the plurality of lateral ties are at least partially disengagable and re-engagable to provide access to the ulcer or skin defect for care.

10. The device of claim 1, wherein the plurality of lateral ties are at least partially adjustable to reduce a separation distance between respective inside lateral edges of the first panel and the second panel and apply a compressive force to tissue therebetween when the device is adhered to skin.

11. The device of claim 1, wherein one or more edges of the first panel and the second panel is sinusoidal or scalloped to minimize or distribute shear force or minimize skin blister formation.

12. The device of claim 1, wherein the first panel comprises a plurality of perforations that extend in a direction that is parallel to an inner edge of the first panel, and
wherein the second panel comprises a plurality of perforations that extend in a direction that is parallel to an inner edge of the second panel.

13. A closure device for treating an ulcer or skin defect, the closure device comprising:
a first panel having a first adhesive bottom surface for adhering to skin on a first side of an ulcer or skin defect;
a second panel having a second adhesive bottom surface for adhering to skin on a second side of the ulcer or skin defect,
a plurality of lateral ties coupling the first and second panels to one another, wherein the first panel and the second panel have respective longitudinal axes; and
a plurality of liners coupled to the first and second adhesive bottom surfaces,
wherein the plurality of liners are aligned in an orientation transverse to the respective longitudinal axes of the first panel and the second panel,
wherein the plurality of liners comprise a middle liner positioned between a first adjacent liner and a second adjacent liner,
wherein the middle liner is configured to be removed from the first panel and the second panel prior to removal of the first adjacent liner and the second adjacent liner, and
wherein the middle liner has a tapered shape such that the middle liner covers a portion of the first panel and a portion of the second panel prior to being removed from the first panel and the second panel, and
wherein a surface area of the portion of the first panel that is covered by the middle liner is greater than a surface area of the portion of the second panel that is covered by the middle liner.

14. The closure device of claim 13, wherein the first panel comprises a first base layer,
wherein the second panel comprises a second base layer,
wherein the first panel and the second panel each further comprise one or more force distribution structures coupled to the first base layer and the second base layer, respectively, and
wherein the one or more force distribution structures are more rigid than the first base layer and the second base layer.

15. The closure device of claim 13, wherein the plurality of lateral ties are at least partially elastic.

16. The closure device of claim 15, wherein the plurality of lateral ties comprise an elastic or spring component.

17. The closure device of claim 16, wherein the elastic or spring component has a serpentine configuration that couples the plurality of lateral ties to each other at a position between the first panel and the second panel.

18. The closure device of claim 16, wherein the plurality of lateral ties are at least partially disengagable and re-engagable to provide access to the ulcer or skin defect for care.

19. The closure device of claim 13, wherein the plurality of lateral ties are at least partially adjustable to reduce a separation distance between respective inside lateral edges of the first panel and the second panel and apply a compressive force to tissue therebetween when the closure device is adhered to skin.

20. The closure device of claim 13, wherein one or more edges of the first panel and the second panel is sinusoidal or scalloped to minimize or distribute shear force or minimize skin blister formation.

* * * * *